United States Patent
Vermaas et al.

(10) Patent No.: US 10,118,173 B2
(45) Date of Patent: Nov. 6, 2018

(54) METHOD AND DEVICE FOR SEPARATING IMMISCIBLE LIQUIDS TO EFFECTIVELY ISOLATE AT LEAST ONE OF THE LIQUIDS

(71) Applicant: Illumina, Inc., San Diego, CA (US)

(72) Inventors: Eric Hans Vermaas, San Diego, CA (US); Matthew Hage, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 112 days.

(21) Appl. No.: 14/879,930

(22) Filed: Oct. 9, 2015

(65) Prior Publication Data
US 2016/0101420 A1    Apr. 14, 2016

Related U.S. Application Data

(60) Provisional application No. 62/062,134, filed on Oct. 9, 2014.

(51) Int. Cl.
*B01D 35/00* (2006.01)
*G01N 1/18* (2006.01)
(Continued)

(52) U.S. Cl.
CPC .... *B01L 3/502784* (2013.01); *B01D 17/0202* (2013.01); *B01D 17/0214* (2013.01);
(Continued)

(58) Field of Classification Search
CPC ............. G01N 1/18; G01N 1/00; B01D 35/00
(Continued)

(56) References Cited

U.S. PATENT DOCUMENTS 3,880,739 A * 4/1975 Leavitt .................. B01D 61/02
435/147
4,414,280 A * 11/1983 Silva .................. B01D 67/0011
204/296
(Continued)

FOREIGN PATENT DOCUMENTS

EP    1955656    8/2008
WO   0181566    11/2001
(Continued)

OTHER PUBLICATIONS

Dhindsa, et al "Virtual Electrowetting Channels: Electronic Liquid Transport with Continuous Channel Functionality," Lab Chip, 10:832-836.
(Continued)

*Primary Examiner* — Brian J. Sines
(74) *Attorney, Agent, or Firm* — Illumina, Inc.

(57) ABSTRACT

Method that includes providing a phase-separation device having a porous membrane with a filter surface. The filter surface has a non-planar contour that forms a receiving cavity. The method also includes providing a liquid mixture into the receiving cavity of the porous membrane. The liquid mixture includes a polar liquid and a non-polar liquid that are immiscible with respect to each other. The filter surface along the receiving cavity has a surface energy that impedes flow of the polar liquid through the filter surface and permit flow of the non-polar liquid into the porous membrane. The method also includes permitting the non-polar liquid to flow into the porous membrane. The polar liquid forms a droplet within the receiving cavity as the non-polar liquid flows into the porous membrane.

21 Claims, 13 Drawing Sheets

(51) Int. Cl.
*G01N 1/00* (2006.01)
*B01L 3/00* (2006.01)
*B01D 17/02* (2006.01)
*B01D 17/00* (2006.01)
*B01D 63/08* (2006.01)
*B01D 69/02* (2006.01)
*B01D 71/36* (2006.01)
*C12Q 1/6806* (2018.01)

(52) U.S. Cl.
CPC ......... *B01D 17/085* (2013.01); *B01D 63/088* (2013.01); *B01D 69/02* (2013.01); *B01D 71/36* (2013.01); *B01L 3/50255* (2013.01); *B01D 2325/38* (2013.01); *B01L 2200/0673* (2013.01); *B01L 2200/10* (2013.01); *B01L 2300/0681* (2013.01); *B01L 2300/0816* (2013.01); *B01L 2300/12* (2013.01); *B01L 2300/165* (2013.01); *B01L 2400/0406* (2013.01); *B01L 2400/0409* (2013.01); *C12Q 1/6806* (2013.01)

(58) Field of Classification Search
USPC ......... 422/68.1, 502, 503, 504, 534; 436/43, 436/177, 180, 175, 178; 210/644, 645, 210/649, 650
See application file for complete search history.

(56) References Cited

U.S. PATENT DOCUMENTS

| | | | |
|---|---|---|---|
| 4,780,211 A * | 10/1988 | Lien | B01D 17/085 210/644 |
| 5,528,050 A | 6/1996 | Miller et al. | |
| 5,641,658 A | 6/1997 | Adams et al. | |
| 5,719,391 A | 2/1998 | Kain | |
| 5,851,491 A | 12/1998 | Moulton | |
| 6,045,757 A | 4/2000 | Moriarty et al. | |
| 6,086,768 A | 7/2000 | Sims | |
| 6,090,592 A | 7/2000 | Adams et al. | |
| 6,117,394 A | 9/2000 | Smith | |
| 6,183,645 B1 | 2/2001 | DeWitt | |
| 6,565,727 B1 | 5/2003 | Kim et al. | |
| 6,773,566 B2 | 8/2004 | Shenderov | |
| 6,911,132 B2 | 6/2005 | Pamula et al. | |
| 6,977,033 B2 | 12/2005 | Decre et al. | |
| 7,052,244 B2 | 5/2006 | Marchand et al. | |
| 7,057,026 B2 | 6/2006 | Kozlov et al. | |
| 7,115,400 B1 | 10/2006 | Adessi et al. | |
| 7,163,612 B2 | 1/2007 | Becker et al. | |
| 7,211,414 B2 | 5/2007 | Turner et al. | |
| 7,315,019 B2 | 1/2008 | Xu et al. | |
| 7,328,979 B2 | 2/2008 | Yamakawa et al. | |
| 7,329,492 B2 | 2/2008 | HArdin et al. | |
| 7,405,281 B2 | 7/2008 | Ranket et al. | |
| 7,547,380 B2 | 6/2009 | Sterling et al. | |
| 7,641,779 B2 | 1/2010 | Becker et al. | |
| 7,727,466 B2 | 6/2010 | Meathrel et al. | |
| 7,985,343 B2 | 7/2011 | Haldopoulos et al. | |
| 8,141,717 B2 | 3/2012 | Wingo et al. | |
| 8,158,926 B2 | 4/2012 | Feng et al. | |
| 8,241,573 B2 | 8/2012 | Banerjee et al. | |
| 8,563,477 B2 | 10/2013 | Smith et al. | |
| 8,748,789 B2 | 6/2014 | Triener et al. | |
| 8,951,781 B2 | 2/2015 | Reed et al. | |
| 9,190,736 B1 * | 11/2015 | Burckel | H01Q 7/00 |
| 2002/0055100 A1 | 5/2002 | Kawashima | |
| 2003/0098121 A1 | 5/2003 | Moya | |
| 2003/0150792 A1* | 8/2003 | Koehler | B29C 66/1122 210/321.84 |
| 2003/0205632 A1 | 11/2003 | Kim et al. | |
| 2004/0002090 A1 | 1/2004 | Mayer et al. | |
| 2004/0096853 A1 | 5/2004 | Mayer | |
| 2004/0126796 A1* | 7/2004 | Carlson | C12N 15/1003 435/6.11 |
| 2005/0179746 A1 | 8/2005 | Dhindsa et al. | |
| 2006/0039823 A1 | 2/2006 | Wu | |
| 2006/0164490 A1 | 7/2006 | Kim et al. | |
| 2006/0194331 A1 | 8/2006 | Pollack et al. | |
| 2007/0023292 A1 | 2/2007 | Shah et al. | |
| 2007/0128624 A1 | 6/2007 | Gormley | |
| 2007/0275415 A1 | 11/2007 | Srinivasan et al. | |
| 2008/0009420 A1 | 1/2008 | Schroth et al. | |
| 2008/0108082 A1 | 5/2008 | Rank et al. | |
| 2008/0124252 A1 | 5/2008 | Adachi et al. | |
| 2008/0283414 A1 | 11/2008 | Monroe et al. | |
| 2009/0131543 A1 | 5/2009 | Weitz et al. | |
| 2009/0192044 A1 | 7/2009 | Fouillett et al. | |
| 2009/0239308 A1 | 9/2009 | Dube et al. | |
| 2009/0283407 A1 | 11/2009 | Kim et al. | |
| 2009/0321262 A1 | 12/2009 | Roux et al. | |
| 2010/0089186 A1 | 4/2010 | Babcock et al. | |
| 2010/0096266 A1 | 4/2010 | Velev | |
| 2010/0137163 A1 | 6/2010 | Link et al. | |
| 2010/0173394 A1 | 7/2010 | Colston et al. | |
| 2010/0291578 A1 | 11/2010 | Pollack et al. | |
| 2011/0059865 A1 | 3/2011 | Smith et al. | |
| 2011/0118132 A1 | 5/2011 | Winger et al. | |
| 2012/0270305 A1 | 10/2012 | Reed et al. | |
| 2013/0023422 A1 | 1/2013 | Feng et al. | |
| 2013/0092539 A1 | 4/2013 | Pollack et al. | |
| 2013/0099018 A1 | 4/2013 | Miller et al. | |
| 2013/0164742 A1 | 6/2013 | Pollack et al. | |
| 2013/0178374 A1 | 7/2013 | Eckhardt et al. | |
| 2013/0203606 A1 | 8/2013 | Pollack et al. | |
| 2013/0225450 A1 | 8/2013 | Pollack et al. | |
| 2013/0225452 A1 | 8/2013 | Pollack et al. | |
| 2013/0260372 A1 | 10/2013 | Buermann et al. | |
| 2013/0323732 A1 | 12/2013 | Anderson et al. | |
| 2014/0079923 A1 | 3/2014 | George et al. | |
| 2014/0147627 A1* | 5/2014 | Aizenberg | A61L 15/24 428/141 |
| 2014/0216579 A1 | 8/2014 | Bemis et al. | |
| 2014/0231259 A1 | 8/2014 | Srinivasan | |
| 2014/0234873 A1 | 8/2014 | Leck et al. | |
| 2014/0256595 A1 | 9/2014 | Link et al. | |
| 2014/0272996 A1 | 9/2014 | Bemis | |

FOREIGN PATENT DOCUMENTS

| | | |
|---|---|---|
| WO | 2002080822 | 10/2002 |
| WO | 07010251 | 1/2007 |
| WO | 2007120241 | 10/2007 |
| WO | 2007123744 | 11/2007 |
| WO | 2008042067 | 4/2008 |
| WO | 2008101194 | 8/2008 |
| WO | 2009003184 | 12/2008 |
| WO | 2008098236 | 1/2009 |
| WO | 2009021173 | 2/2009 |
| WO | 2010027894 | 3/2010 |
| WO | 2010120977 | 10/2010 |
| WO | 2011002957 | 1/2011 |
| WO | 2013117595 | 8/2013 |
| WO | 2013131962 | 9/2013 |
| WO | 2014064542 | 5/2014 |

OTHER PUBLICATIONS

Souhaimi et al., Membrane Distillation: Principles and Applications, Chapter 8, Membrane Characterization, Elsevier (2011).
Nakao, Determination of Pore Size and Pore Size Distribution. 3. Filtration Membranes: Review, J. Membr. Sci., 96 (1994) 131-165.
Bentley et al, Nature 456:53-59 (2008).
Gjelstad et al "Parallel artificial liquid membrane extraction; microscale liquid-liquid-liquid extraction in the 96 well format," Bioanalysis, 2013, vol. 5, pp. 1377-1385.
Bormashenko, E. et al., "Honeycomb structures obtained with breath figures self-assembly allow water/oil separation", Colloids and Surfaces A: Physicochemical and Engineering Aspects, vol. 415, Dec. 1, 2012, 394-398.

(56) References Cited

OTHER PUBLICATIONS

Du, C. et al., "Durable superhydrophobic and superoleophilic filter paper for oil-water separation prepared by a colloidal deposition method," Applied Surface Science, vol. 313, Jun. 5, 2014, 304-310.
Sartorius Stedim, "Filtrierpapiere fuer Labor und Industrie", https://logismarketat.cdnwm.com/ip/sartorius-filterpapiere-broschuere-filtrierpapiere-fuer-labor-und-industrie-922900.pdf, [retrieved on Apr. 25, 2018], Dec. 31, 2011, 32 pages.
EP Patent Application No. 15848762.9, Partial Supplementary European Search Report dated May 4, 2018, 6 pages.

\* cited by examiner

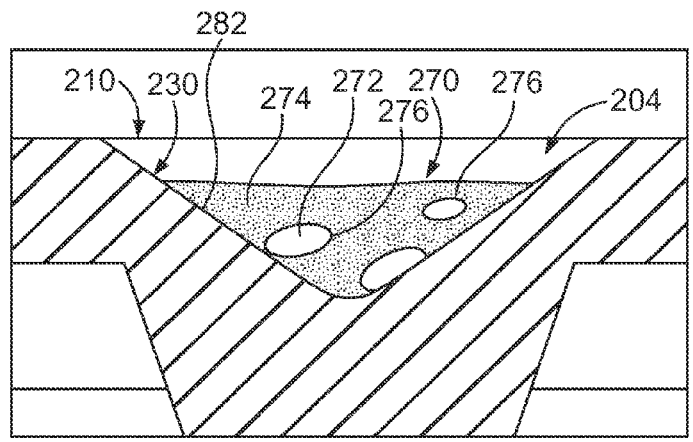
FIG. 8
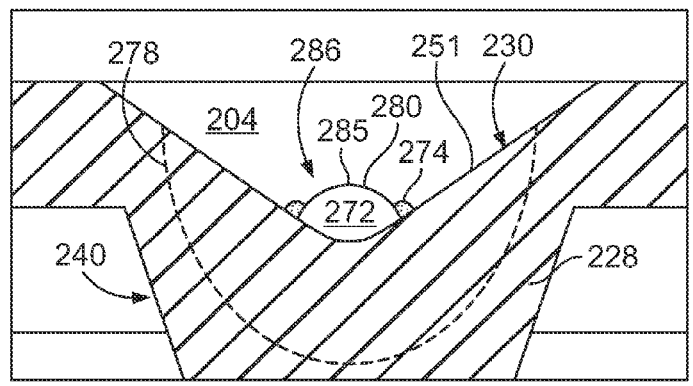
FIG. 9
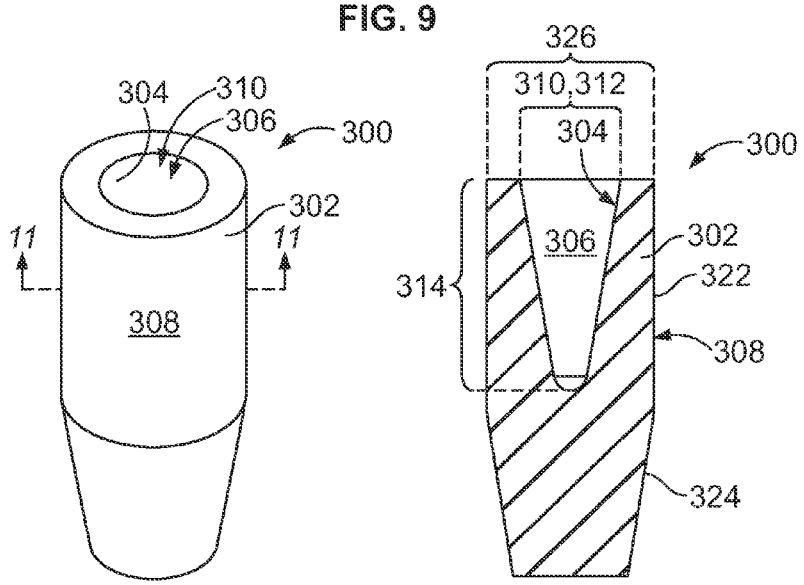
FIG. 10
FIG. 11

METHOD AND DEVICE FOR SEPARATING IMMISCIBLE LIQUIDS TO EFFECTIVELY ISOLATE AT LEAST ONE OF THE LIQUIDS

CROSS-REFERENCE TO RELATED APPLICATION

The present application claims the benefit of U.S. Provisional Application No. 62/062,134, which was filed on Oct. 9, 2014 and is incorporated herein by reference in its entirety.

BACKGROUND

The subject matter herein relates generally to systems and methods for separating immiscible liquids and, more specifically, to systems and methods that effectively isolate at least one of the liquids so that the liquid(s) may be analyzed and/or used in an assay.

Various protocols in biological or chemical analysis involve performing a large number of controlled reactions. The designated reactions may be performed to prepare and/or analyze a biological substance. Digital fluidics (DF) is one technology that may be used to perform such reactions. In DF technology, aqueous droplets may be moved or manipulated (e.g., combined or divided) using electrowetting-mediated operations. For example, a DF device may include a cartridge having an enclosed cavity that is defined by one or more substrates. An array of electrodes may be arranged along the substrate(s) and positioned adjacent to the cavity. The cavity may be filled with a filler liquid (e.g., oil) that is immiscible with respect to the aqueous droplets. The electrodes are configured to provide different electric fields in accordance with a predetermined sequence or schedule to transport, mix, filter, monitor, and/or analyze the aqueous droplets within the DF device. The predetermined sequence may subject the aqueous droplets to designated reactions in order to, for example, prepare a biological substance.

Complex steps may be implemented to control the aqueous droplets and prepare the desired biological substance. As one example, DF technology may be used to prepare libraries of fragmented nucleic acids for next generation sequencing (NGS). After conducting the designated reactions, the droplets may be transported to different locations within the DF device that are accessible to the user. The user may remove each droplet by, for example, inserting a pipettor into the cavity and withdrawing a small volume (e.g., 20 µl) that includes both the aqueous solution and the filler liquid. Often, the aqueous solution is a fraction of the entire liquid with the filler liquid forming a majority of the liquid. For example, a volume of the filler liquid may be two time (2×), ten times (10×), or twenty times (20×) the volume of the aqueous solution.

For some applications, it may be necessary to separate the aqueous solution from the filler liquid so that the aqueous solution may be used in an assay or may be recovered at the end of an assay or workflow. Separating small volumes of liquid from other liquids in a reliable and efficient manner, however, can be challenging. One conventional method for separating a liquid mixture that includes an aqueous solution and a filler liquid includes depositing the mixture into a well and spinning the well in a centrifuge to separate the liquids into different layers. The layer of the filler liquid may form on top of the layer of the aqueous solution. The layer of the filler liquid may be removed with a pipettor or through decanting. For particular protocols, this separation process may take 45 minutes or longer. Moreover, the process can be messy and unpredictable, especially when working with several different samples.

Accordingly, there is a need for a method of separating two or more immiscible liquids in a manner that is at least one of quicker, more efficient, or more reliable than known separation processes.

BRIEF DESCRIPTION

In an embodiment, a method is provided that includes providing a phase-separation device having a porous membrane with a filter surface. The filter surface has a non-planar contour that forms a receiving cavity. The method also includes providing a liquid mixture into the receiving cavity of the porous membrane. The liquid mixture includes a polar liquid and a non-polar liquid that are immiscible with respect to each other. The filter surface along the receiving cavity has a surface energy that impedes flow of the polar liquid through the filter surface and permit flow of the non-polar liquid into the porous membrane. The method also includes permitting the non-polar liquid to flow into the porous membrane. The polar liquid forms a droplet within the receiving cavity as the non-polar liquid flows into the porous membrane.

In an embodiment, a phase-separation device is provided that includes a porous membrane having a filter surface. The filter surface has a non-planar contour that forms a receiving cavity, wherein the filter surface along the receiving cavity impedes absorption of a polar liquid but permits absorption of a non-polar liquid into the porous membrane.

In an embodiment, a method is provided that includes providing a phase-separation device including a porous membrane having a filter surface. The filter surface has a non-planar contour that forms a receiving cavity. The method also includes depositing a liquid mixture into the receiving cavity of the porous membrane. The liquid mixture includes a first liquid and a second liquid that are immiscible with respect to each other. The filter surface along the receiving cavity is configured to impede flow of the first liquid through the filter surface and permit flow of the second liquid into the porous membrane. The method also includes permitting the second liquid to flow into the porous membrane. The first liquid forms a droplet within the receiving cavity as the second liquid flows into the porous membrane.

In an embodiment, an assay system is provided that includes a sample preparation system configured to prepare a liquid mixture having a polar liquid and a non-polar liquid that are immiscible with respect to each other. The assay system also includes a phase-separation device having a porous membrane having a filter surface. The filter surface has a non-planar contour that forms a receiving cavity configured to receive the liquid mixture. The filter surface along the receiving cavity is configured to impede flow of the polar liquid through the filter surface and permit flow of the non-polar liquid into the porous membrane such that the polar liquid forms a droplet within the receiving cavity as the non-polar liquid flows into the porous membrane.

In an embodiment, an assay system is provided that includes a phase-separation device including a porous membrane having a filter surface. The filter surface has a non-planar contour that forms a receiving cavity configured to receive a liquid mixture. The liquid mixture has a polar liquid and a non-polar liquid that are immiscible with respect to each other, wherein the filter surface along the receiving cavity is configured to impede flow of the polar liquid through the filter surface and permit flow of the non-polar liquid into the porous membrane such that the polar liquid forms a droplet within the receiving cavity as the non-polar liquid flows into the porous membrane. The assay system also includes an analysis system configured to perform one or more assay protocols utilizing the droplet of the polar liquid.

In an embodiment, an assay system is provided that includes a sample preparation system configured to prepare a liquid mixture having a first liquid and a second liquid that are immiscible with respect to each other. The assay system also includes a phase-separation device having a porous membrane having a filter surface. The filter surface has a non-planar contour that forms a receiving cavity configured to receive the liquid mixture. The filter surface along the receiving cavity is configured to impede flow of the first liquid through the filter surface and permit flow of the second liquid into the porous membrane such that the first liquid forms a droplet within the receiving cavity as the second liquid flows into the porous membrane.

In an embodiment, an assay system is provided that includes a phase-separation device including a porous membrane having a filter surface. The filter surface has a non-planar contour that forms a receiving cavity configured to receive a liquid mixture. The liquid mixture has a first liquid and a second liquid that are immiscible with respect to each other, wherein the filter surface along the receiving cavity is configured to impede flow of the first liquid through the filter surface and permit flow of the second liquid into the porous membrane such that the first liquid forms a droplet within the receiving cavity as the second liquid flows into the porous membrane. The assay system also includes an analysis system configured to perform one or more assay protocols utilizing the droplet of the first liquid.

BRIEF DESCRIPTION OF THE DRAWINGS

FIG. 8 is a cross-section of the receiving cavity at a first stage of a filtering or separation process.

FIG. 9 is a cross-section of the receiving cavity at a later second stage of the filtering or separation process.

FIG. 10 is a perspective view of a filter body in accordance with an embodiment.

FIG. 11 is a cross-section of the filter body taken along the line 11-11 in FIG. 10.

DETAILED DESCRIPTION

Figure 2:
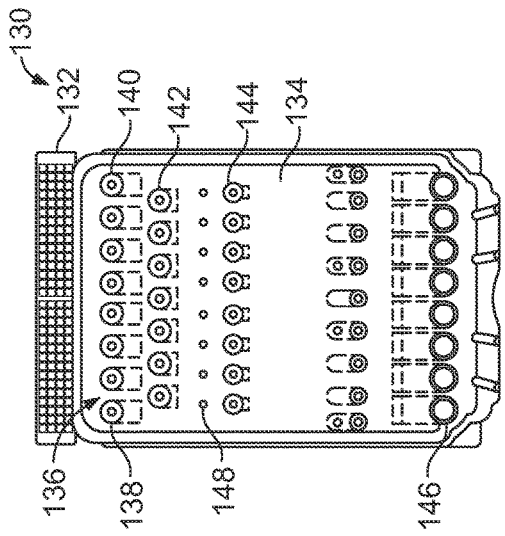
FIG. 2 illustrates a plan view of a fluidic system that may be used with the assay system of FIG. 1.

Embodiments set forth herein may be used in various applications in which the separation of immiscible liquids is desired. In particular embodiments, at least one of the immiscible liquids is subsequently analyzed and/or used to prepare a designated substance. For example, the immiscible liquids may include a polar liquid (e.g., aqueous solution) and a non-polar liquid (e.g., oil). The immiscible liquids may be combined within a liquid mixture. In some cases, the immiscible liquids may be used to carry out one or more operations, such as one or more designated reactions with one of the liquids. In particular embodiments, the polar liquid includes a biological substance that is subsequently used and/or analyzed by the user. For instance, the polar liquid may include a library of fragmented nucleic acids that is used for sequencing-by-synthesis (SBS). The library of fragmented nucleic acids may be prepared using a library-preparation protocol, such as one or more protocols described in U.S. Patent Publication Nos. 2013/0203606 and 2013/0225452, each of which is incorporated herein by reference in its entirety.

Embodiments set forth herein may separate the immiscible liquids. For example, the liquid mixture may be provided into a common space (e.g., a receiving cavity) that is defined by a porous membrane. The porous membrane may permit at least one of the immiscible liquids to flow through the porous membrane while impeding at least one other immiscible liquid from flowing into the porous membrane. The remaining liquid may pool within the common space. If the remaining liquid includes a polar liquid, intermolecular forces, such as forces generated by hydrogen bonding and Van der Waals interactions, may cause molecules of the polar liquid to gather or unite into a larger volume (e.g., droplet). The larger volume of polar liquid may then be removed and used for other operations. In some cases, the surface of the porous membrane may be shaped and/or have certain properties that cause the polar liquid to bead within the common space. The bead may provide a designated volume of the polar liquid that is easier to locate and remove compared to liquids that do not bead.

As used herein, a "liquid" is a substance that is relatively incompressible and has a capacity to flow and to substantially conform to a shape of a container or a surface that holds the substance. A liquid may be aqueous based and include polar molecules exhibiting surface tension that holds the liquid together. A liquid may also include non-polar molecules, such as in an oil-based or non-aqueous substance. It is understood that references to a liquid in the present application may include a liquid that was formed from the combination of two or more liquids. For example, separate miscible solutions may be combined into a single liquid.

As used herein, the term "immiscible" is used to describe liquids that are substantially incapable of dissolving into each other or being mixed with each other to form a homogeneous liquid at predetermined conditions. The predetermined conditions may be ambient conditions, such as between 15° C. and 30° C. and about 1.0 atm. However, other conditions may be provided to facilitate separation of the different liquids. When combined together in a confined space, immiscible fluids may separate into at least two phases, wherein each phase contains at least 90%, at least 95%, at least 99.0%, or at least 99.5% of a single fluid. In addition, the term "immiscible" is intended to encompass liquids that remain in separate fluid phases over an extended period of time but may eventually mix. For example, immiscible fluids may remain in essentially separate fluid phases for at least ten minutes, for at least twenty minutes, or for at least thirty minutes. In some embodiments, the immiscible fluids may remain in essentially separate fluid phases for at least one hour, at least twelve hours, or at least twenty-four hours. Immiscible liquids may have different densities such that one fluid phase typically forms above or below another fluid phase. For example, in some embodiments, non-polar liquids may rise above polar liquids. Immiscible liquids may mix to form a heterogeneous liquid such as an emulsion.

Liquids, including droplets of liquids, may experience different forces in various embodiments. Such forces may include cohesive forces (i.e., attractive forces between like molecules of the liquid) and adhesive forces (i.e., attractive forces between molecules of the liquid and a solid surface or vapor that surrounds the liquid). Cohesive and adhesive forces arise from the interaction of atoms and molecules that are located along, for example, a liquid-vapor interface and a liquid-solid interface. Another force that affects the flow of liquid in embodiments describe herein is gravity (or gravitational force) that is experienced by the liquid-of-interest but also other substances. Embodiments set forth herein may utilize these forces to separate immiscible liquids and effectively isolate at least one of the liquids so that the liquid(s) may be used in a subsequent task or operation.

A liquid may have different wetting characteristics or properties based on properties of the surface that contacts the liquid. More specifically, a droplet of a liquid may have a contact angle that is based on properties of the liquid and the solid surface. A contact angle is the angle formed by the intersection of two planes tangent to the droplet and the corresponding solid surface that the droplet rests upon. The contact angle indicates a wetting ability of the liquid to the surface. Wetting is a liquid's ability to spread along a solid surface. The wetting of a solid surface by a liquid is controlled by the intermolecular interactions of molecules along an interface between the two phases. If the adhesive forces are relatively greater than the cohesive forces, the wetting of the liquid to the surface is greater (i.e., the contact angle will be relatively small). If the cohesive forces are relatively greater than the adhesive forces, the wetting of the liquid to the surface is smaller (i.e., the contact angle will be relatively large). When the contact angle is large, the liquid appears to form a bead along the surface.

Surface tension in a liquid is caused by the cohesive forces of the liquid and, as such, can have an affect on the contact angle. As the surface tension increases, an ability of the liquid to reduce its surface area (i.e., bead up) also increases. Surfaces of solids, however, may be characterized as having a surface energy. As the surface energy of a solid increases, the ability of the solid to interact with the liquid also increases (i.e., the contact angle decreases). As an example, when a liquid of low surface tension is placed on a solid of high surface energy, the liquid spreads across the surface and has a small contact angle. If a liquid has a high surface tension and is placed on a surface of low surface energy, the liquid may form a bead on the surface and have a high contact angle. As described herein, the beading of a liquid within a receiving cavity may be, in part, based on the surface tension of the liquid and the surface energy of the solid surface that holds the liquid.

Likewise, the ability of a liquid to flow into a porous membrane may be primarily determined by at least one of (a) the surface tension of the liquid (or lack thereof); (b) the surface energy of the solid surface; (c) a mean pore size of the porous membrane; and (d) a porosity of the porous membrane. For example, the porous membrane may have a surface energy, a porosity, and a mean pore size that collectively operate to allow one of the liquids (e.g., non-polar liquid) to flow into the porous membrane while another liquid (e.g., polar liquid) forms a droplet within the receiving cavity. A shape of the solid surface may also facilitate flow of one liquid and/or droplet forming of the other liquid. Accordingly, embodiments described herein may utilize inherent properties of liquids (e.g., the surface tension), inherent properties of a solid surface (e.g., surface energy) that contact the liquids, and a shape of the solid surface to control the flow of the liquids. Collectively, these parameters may allow one liquid to flow into a porous membrane but impede flow of the other liquid into the porous membrane and, optionally, facilitate beading of the other liquid.

It is noted that other factors may affect the contact angle or the wetting of a liquid to a solid and whether a liquid flows into a porous membrane. For example, purity of the liquid or whether a surfactant is used may affect the surface tension of the liquid and the molecular interactions along the solid-liquid interface. Purity of the solid (e.g., porous membrane) or whether a coating is placed on the solid surface may affect the surface energy of a solid. Also, temperature of the environment, composition of the surrounding air, and the roughness or smoothness of the surface may all affect the interactions between the liquid and the solid surface. The concepts discussed above are discussed in greater detail in *Surfaces, Interfaces, and Colloids: Principles and Applications, Second Edition*, Drew Meyers, 1999, John Wiley & Sons, Inc. and in *Contact Angle, Wettability, and Adhesion*, edited by Robert F. Gould (1964), both of which are hereby incorporated by reference.

Certain embodiments may utilize DF technology, which may also be referred to as digital microfluidics (DMF) or electrowetting-on-dielectric (EWOD). However, embodiments set forth herein are not limited to DF applications and may be used in other systems that use immiscible liquids. Embodiments may include distributed assay systems in which one or more liquids is manually carried by a person and/or automatically carried by a machine to other locations of the assay system. Embodiments may also include assay systems that are essentially closed systems, such as lab-on-chip (LOC) devices or micro-electro-mechanical systems (MEMS) devices. In some embodiments, the systems may be single-use disposable devices, such as point-of-care (POC) devices.

As used herein, a "designated reaction" includes a change in at least one of a chemical, electrical, physical, or optical property (or quality). More generally, the designated reaction may be a chemical transformation, chemical change, or chemical interaction. Exemplary reactions include, but are not limited to, chemical reactions such as reduction, oxidation, addition, elimination, rearrangement, esterification, amidation, etherification, cyclization, or substitution; binding interactions in which a first chemical binds to a second chemical; dissociation reactions in which two or more chemicals detach from each other; fluorescence; luminescence; bioluminescence; chemiluminescence; and biological reactions, such as nucleic acid replication, nucleic acid amplification, nucleic acid hybridization, nucleic acid ligation, phosphorylation, enzymatic catalysis, receptor binding, or ligand binding.

The designated reactions may prepare a biological substance for subsequent utilization and/or subsequent analysis in an assay protocol. In particular embodiments, the designated reactions may prepare a library of nucleic acid fragments. Documents that describe preparation of a biological sample using DF technology include U.S. Patent Publication Nos. 2013/0203606; 2013/0225452; 2010/0291578; 2013/0164742 2013/0092539; 2013/0178374; 2013/0225450; 2007/0275415; and 2013/0092539, each of which is incorporated herein by reference in its entirety.

In some embodiments, the designated reaction includes the incorporation of a fluorescently-labeled molecule to an analyte. The analyte may be an oligonucleotide and the fluorescently-labeled molecule may be a nucleotide. The designated reaction may be detected when an excitation light is directed toward the oligonucleotide having the labeled nucleotide, and the fluorophore emits a detectable fluorescent signal. In alternative embodiments, the detected fluorescence is a result of chemiluminescence or bioluminescence. A designated reaction may also increase fluorescence (or Förster) resonance energy transfer (FRET), for example, by bringing a donor fluorophore in proximity to an acceptor fluorophore, decrease FRET by separating donor and acceptor fluorophores, increase fluorescence by separating a quencher from a fluorophore or decrease fluorescence by co-locating a quencher and fluorophore.

As used herein, the term "immobilized," when used with respect to a biomolecule or biochemical substance, includes substantially attaching the biomolecule or biochemical substance at a molecular level to a surface. For example, a biomolecule or biochemical substance may be immobilized to a surface of the substrate material using adsorption techniques including non-covalent interactions (e.g., electrostatic forces, van der Waals, and dehydration of hydrophobic interfaces) and covalent binding techniques where functional groups or linkers facilitate attaching the biomolecules to the surface. Immobilizing biomolecules or biochemical substances to a surface of a substrate material may be based upon the properties of the substrate surface, the liquid medium carrying the biomolecule or biochemical substance, and the properties of the biomolecules or biochemical substances themselves. In some cases, a substrate surface may be functionalized (e.g., chemically or physically modified) to facilitate immobilizing the biomolecules (or biological or chemical substances) to the substrate surface. The substrate surface may be first modified to have functional groups bound to the surface. The functional groups may then bind to biomolecules or biological or chemical substances to immobilize them thereon. A substance can be immobilized to a surface via a gel, for example, as described in U.S. Pat. No. 8,563,477; US Patent Publ. No. 2011/0059865 A1 or US Patent Publ. No. 2014/0079923 A1, each of which is incorporated herein by reference.

In some embodiments, nucleic acids can be attached to a surface and amplified using bridge amplification. Useful bridge amplification methods are described, for example, in U.S. Pat. No. 5,641,658; WO 07/010251, U.S. Pat. No. 6,090,592; U.S. Patent Publ. No. 2002/0055100 A1; U.S. Pat. No. 7,115,400; U.S. Patent Publ. No. 2004/0096853 A1; U.S. Patent Publ. No. 2004/0002090 A1; U.S. Patent Publ. No. 2007/0128624 A1; and U.S. Patent Publ. No. 2008/0009420 A1, each of which is incorporated herein in its entirety. Another useful method for amplifying nucleic acids on a surface is rolling circle amplification (RCA), for example, using methods set forth in further detail below. In some embodiments, the nucleic acids can be attached to a surface and amplified using one or more primer pairs. For example, one of the primers can be in solution and the other primer can be immobilized on the surface (e.g., 5'-attached). By way of example, a nucleic acid molecule can hybridize to one of the primers on the surface followed by extension of the immobilized primer to produce a first copy of the nucleic acid. The primer in solution then hybridizes to the first copy of the nucleic acid which can be extended using the first copy of the nucleic acid as a template. Optionally, after the first copy of the nucleic acid is produced, the original nucleic acid molecule can hybridize to a second immobilized primer on the surface and can be extended at the same time or after the primer in solution is extended. In any embodiment, repeated rounds of extension (e.g., amplification) using the immobilized primer and primer in solution provide multiple copies of the nucleic acid.

As used herein, the term "droplet" includes a relatively small volume of a liquid (or liquids) (e.g., less than 1 ml) that has a three-dimensional shape that is defined by at least one of inherent properties of the liquid(s) (e.g., cohesive forces), a shape of a surface that contacts the liquid(s), or properties of the surface that contacts the liquid(s). The droplet may have an external surface that has a curved contour. For example, the external surface may have a convex shape.

In some circumstances, a droplet may be at least partially bounded by another liquid. For example, a droplet may be completely surrounded by a filler liquid within a DF device or may be bounded by a filler liquid and one or more surfaces of the DF device. As another example, a droplet may be bounded by filler liquid, one or more surfaces of the DF device, and/or the atmosphere. As yet another example, a droplet may be bounded by filler liquid and the atmosphere. Droplets may, for example, be aqueous or non-aqueous or may be mixtures or emulsions including aqueous and non-aqueous components. Droplets may take a wide variety of shapes. Non-limiting examples include being generally disc shaped, slug shaped, a truncated sphere, an ellipsoid, spherical, a partially compressed sphere, hemispherical, an ovoid, cylindrical, combinations thereof, and various shapes formed during droplet operations, such as merging or splitting or formed as a result of contact of such shapes with one or more surfaces of a droplet actuator.

In various embodiments, a droplet may include a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes. Moreover, a droplet may include a reagent, such as water, deionized water, saline solutions, acidic solutions, basic solutions, detergent solutions and/or buffers. A droplet can include nucleic acids, such as DNA, genomic DNA, RNA, mRNA or analogs thereof; nucleotides such as deoxyribonucleotides, ribonucleotides or analogs thereof such as analogs having terminator moieties such as those described in Bentley et al., Nature 456:53-59 (2008); Gormley et al., International Patent Pub. No. WO/2013/131962, entitled, "Improved Methods of Nucleic Acid Sequencing," published on Sep. 12, 2013; Barnes et al., U.S. Pat. No. 7,057,026, entitled "Labelled Nucleotides," issued on Jun. 6, 2006; Kozlov et al., International Patent Pub. No. WO/2008/042067, entitled, "Compositions and Methods for Nucleotide Sequencing," published on Apr. 10, 2008; Rigatti et al., International Patent Pub. No. WO/2013/117595, entitled, "Targeted Enrichment and Amplification of Nucleic Acids on a Support," published on Aug. 15, 2013; Hardin et al., U.S. Pat. No. 7,329,492, entitled "Methods for Real-Time Single Molecule Sequence Determination," issued on Feb. 12, 2008; Hardin et al., U.S. Pat. No. 7,211,414, entitled "Enzymatic Nucleic Acid Synthesis: Compositions and Methods for Altering Monomer Incorporation Fidelity," issued on May 1, 2007; Turner et al., U.S. Pat. No. 7,315,019, entitled "Arrays of Optical Confinements and Uses Thereof," issued on Jan. 1, 2008; Xu et al., U.S. Pat. No. 7,405,281, entitled "Fluorescent Nucleotide Analogs and Uses Therefor," issued on Jul. 29, 2008; and Rank et al., U.S. Patent Pub. No. 20080108082, entitled "Polymerase Enzymes and Reagents for Enhanced Nucleic Acid Sequencing," published on May 8, 2008, the entire disclosures of which are incorporated herein by reference; enzymes such as polymerases, ligases, recombinases, or transposases; binding partners such as antibodies, epitopes, streptavidin, avidin, biotin, lectins or carbohydrates; or other biochemically active molecules. Other examples of droplet contents include reagents, such as a reagent for a biochemical protocol, such as a nucleic acid amplification protocol, an affinity-based assay protocol, an enzymatic assay protocol, a sequencing protocol, and/or a protocol for analyses of biological fluids. A droplet may include one or more substrate beads.

As used herein, a "droplet actuator" means a device, system, or assembly that is capable of manipulating droplets. In one or more embodiments, the droplets are manipulated using electrowetting-mediated operations. For examples of droplet actuators, see Pamula et al., U.S. Pat. No. 6,911,132, entitled "Apparatus for Manipulating Droplets by Electrowetting-Based Techniques," issued on Jun. 28, 2005; Pamula et al., U.S. Patent Pub. No. 20060194331, entitled "Apparatuses and Methods for Manipulating Droplets on a Printed Circuit Board," published on Aug. 31, 2006; Pollack et al., International Patent Pub. No. WO/2007/120241, entitled "Droplet-Based Biochemistry," published on Oct. 25, 2007; Shenderov, U.S. Pat. No. 6,773,566, entitled "Electrostatic Actuators for Fluidics and Methods for Using Same," issued on Aug. 10, 2004; Shenderov, U.S. Pat. No. 6,565,727, entitled "Actuators for Fluidics Without Moving Parts," issued on May 20, 2003; Kim et al., U.S. Patent Pub. No. 20030205632, entitled "Electrowetting-driven Micropumping," published on Nov. 6, 2003; Kim et al., U.S. Patent Pub. No. 20060164490, entitled "Method and Apparatus for Promoting the Complete Transfer of Liquid Drops from a Nozzle," published on Jul. 27, 2006; Kim et al., U.S. Patent Pub. No. 20070023292, entitled "Small Object Moving on Printed Circuit Board," published on Feb. 1, 2007; Shah et al., U.S. Patent Pub. No. 20090283407, entitled "Method for Using Magnetic Particles in Droplet Fluidics," published on Nov. 19, 2009; Kim et al., U.S. Patent Pub. No. 20100096266, entitled "Method and Apparatus for Real-time Feedback Control of Electrical Manipulation of Droplets on Chip," published on Apr. 22, 2010; Velev, U.S. Pat. No. 7,547,380, entitled "Droplet Transportation Devices and Methods Having a Liquid Surface," issued on Jun. 16, 2009; Sterling et al., U.S. Pat. No. 7,163,612, entitled "Method, Apparatus and Article for Fluidic Control via Electrowetting, for Chemical, Biochemical and Biological Assays and the Like," issued on Jan. 16, 2007; Becker et al., U.S. Pat. No. 7,641,779, entitled "Method and Apparatus for Programmable Fluidic Processing," issued on Jan. 5, 2010; Becker et al., U.S. Pat. No. 6,977,033, entitled "Method and Apparatus for Programmable Fluidic Processing," issued on Dec. 20, 2005; Decre et al., U.S. Pat. No. 7,328,979, entitled "System for Manipulation of a Body of Fluid," issued on Feb. 12, 2008; Yamakawa et al., U.S. Patent Pub. No. 20060039823, entitled "Chemical Analysis Apparatus," published on Feb. 23, 2006; Wu, International Patent Pub. No. WO/2009/003184, entitled "Digital Fluidics Based Apparatus for Heat-exchanging Chemical Processes," published on Dec. 31, 2008; Fouillet et al., U.S. Patent Pub. No. 20090192044, entitled "Electrode Addressing Method," published on Jul. 30, 2009; Fouillet et al., U.S. Pat. No. 7,052,244, entitled "Device for Displacement of Small Liquid Volumes Along a Micro-catenary Line by Electrostatic Forces," issued on May 30, 2006; Marchand et al., U.S. Patent Pub. No. 20080124252, entitled "Droplet Microreactor," published on May 29, 2008; Adachi et al., U.S. Patent Pub. No. 20090321262, entitled "Liquid Transfer Device," published on Dec. 31, 2009; Roux et al., U.S. Patent Pub. No. 20050179746, entitled "Device for Controlling the Displacement of a Drop Between Two or Several Solid Substrates," published on Aug. 18, 2005; and Dhindsa et al., "Virtual Electrowetting Channels: Electronic Liquid Transport with Continuous Channel Functionality," Lab Chip, 10:832-836 (2010). Each of the above references is incorporated herein by reference in its entirety.

Certain droplet actuators will include one or more substrates arranged with a droplet-operations gap there between and electrodes associated with (e.g., layered on, attached to, and/or embedded in) the one or more substrates and arranged to conduct one or more droplet operations. For example, certain droplet actuators will include a base (or bottom) substrate, electrodes associated with the substrate, one or more dielectric layers atop the substrate and/or electrodes, and optionally one or more hydrophobic layers atop the substrate, dielectric layers and/or the electrodes forming a droplet-operations surface. A top substrate may also be provided, which is separated from the droplet-operations surface by a gap, which may be referred to as a droplet-operations gap. Various electrode arrangements on the top and/or bottom substrates are discussed in the incorporated patents and applications referenced above.

During droplet operations, droplets may remain in continuous contact or frequent contact with a ground or reference electrode. A ground or reference electrode may be associated with the top substrate facing the gap or the bottom substrate facing the gap, or the electrode may be located in the gap. Where electrodes are provided on both substrates, electrical contacts for coupling the electrodes to a droplet actuator instrument for controlling or monitoring the electrodes may be associated with one or both substrates. In some cases, electrodes on one substrate are electrically coupled to the other substrate so that only one substrate is in contact with the droplet actuator. In one embodiment, a conductive material (e.g., an epoxy, such as MASTER BOND™ Polymer System EP79, available from Master Bond, Inc., Hackensack, N.J.) provides the electrical connection between electrodes on one substrate and electrical paths on the other substrates, e.g., a ground electrode on a top substrate may be coupled to an electrical path on a bottom substrate by such a conductive material. Where multiple substrates are used, a spacer may be provided between the substrates to determine the height of the gap therebetween and define on-actuator dispensing reservoirs. The spacer height may, for example, be at least about 5 µm, 100 µm, 200 µm, 250 µm, 275 µm or more. Alternatively or additionally the spacer height may be at most about 600 µm, 400 µm, 350 µm, 300 µm, or less. The spacer may, for example, be formed of a layer of projections form the top or bottom substrates, and/or a material inserted between the top and bottom substrates.

One or more openings or ports may be provided in the one or more substrates for forming a liquid path through which liquid may be delivered into or removed from the droplet-operations gap. The one or more openings may in some cases be aligned for interaction with one or more electrodes, e.g., aligned such that liquid flowed through the opening will come into sufficient proximity with one or more droplet-operations electrodes to permit a droplet operation to be effected by the droplet-operations electrodes using the liquid. The openings may provide access to a receiving cavity where a reservoir of liquid may be stored. The droplet-operations electrodes may be associated with the receiving cavities for controlling the liquid.

The base (or bottom) and top substrates may in some cases be formed as one integral component. One or more reference electrodes may be provided on the base (or bottom) and/or top substrates and/or in the gap. Examples of reference electrode arrangements are provided in the above referenced patents and patent applications, which are incorporated herein by reference in their entireties.

In various embodiments, the manipulation of droplets by a droplet actuator may be electrode mediated, e.g., electrowetting-mediated or dielectrophoresis-mediated or Coulombic-force-mediated. However, embodiments set forth herein are not limited to droplets that are controlled through electrode mediated operations. Examples of other techniques for controlling droplet operations may include using devices that induce hydrodynamic fluidic pressure, such as those that operate on the basis of mechanical principles (e.g. external syringe pumps, pneumatic membrane pumps, vibrating membrane pumps, vacuum devices, centrifugal forces, piezoelectric/ultrasonic pumps and acoustic forces); electrical or magnetic principles (e.g. electroosmotic flow, electrokinetic pumps, ferrofluidic plugs, electrohydrodynamic pumps, attraction or repulsion using magnetic forces and magnetohydrodynamic pumps); thermodynamic principles (e.g. gas bubble generation/phase-change-induced volume expansion); other kinds of surface-wetting principles (e.g. electrowetting, and optoelectrowetting, as well as chemically, thermally, structurally and radioactively induced surface-tension gradients); gravity; surface tension (e.g., capillary action); electrostatic forces (e.g., electroosmotic flow); centrifugal flow (substrate disposed on a compact disc and rotated); magnetic forces (e.g., oscillating ions causes flow); magnetohydrodynamic forces; and vacuum or pressure differential. In certain embodiments, combinations of two or more of the foregoing techniques may be employed to conduct a droplet operation in a droplet actuator of the present disclosure. Similarly, one or more of the foregoing may be used to deliver liquid into a droplet-operations gap, e.g., from a reservoir in another device or from an external reservoir of the droplet actuator (e.g., a reservoir associated with a droplet actuator substrate and a flow path from the reservoir into the droplet-operations gap).

Droplet-operations surfaces of certain droplet actuators may be made from hydrophobic materials or may be coated or treated to make them hydrophobic. For example, in some cases some portion or all of the droplet-operations surfaces may be derivatized with low surface-energy materials or chemistries, e.g., by deposition or using in situ synthesis using compounds such as poly- or per-fluorinated compounds in solution or polymerizable monomers. Examples include TEFLON® AF (available from DuPont, Wilmington, Del.), members of the cytop family of materials, coatings in the FLUOROPEL® family of hydrophobic and superhydrophobic coatings (available from Cytonix Corporation, Beltsville, Md.), silane coatings, fluorosilane coatings, hydrophobic phosphonate derivatives (e.g., those sold by Aculon, Inc), and NOVEC™ electronic coatings (available from 3M Company, St. Paul, Minn.), other fluorinated monomers for plasma-enhanced chemical vapor deposition (PECVD), and organosiloxane (e.g., SiOC) for PECVD. In some cases, the droplet-operations surface may include a hydrophobic coating having a thickness ranging from about 10 nm to about 1,000 nm. Moreover, in some embodiments, the top substrate of the droplet actuator includes an electrically conducting organic polymer, which is then coated with a hydrophobic coating or otherwise treated to make the droplet-operations surface hydrophobic. For example, the electrically conducting organic polymer that is deposited onto a plastic substrate may be poly(3,4-ethylenedioxythiophene) poly(styrenesulfonate) (PEDOT:PSS). Other examples of electrically conducting organic polymers and alternative conductive layers are described in Pollack et al., International Patent Pub. No. WO/2011/002957, entitled "Droplet Actuator Devices and Methods," published on Jan. 6, 2011, the entire disclosure of which is incorporated herein by reference.

One or both substrates of a droplet actuator may be fabricated using a printed circuit board (PCB), glass, indium tin oxide (ITO)-coated glass, and/or semiconductor materials as the substrate. When the substrate is ITO-coated glass, the ITO coating may have a thickness of at least about 20 nm, 50 nm, 75 nm, 100 nm or more. Alternatively or additionally, the thickness can be at most about 200 nm, 150 nm, 125 nm or less. In some cases, the top and/or bottom substrate includes a PCB substrate that is coated with a dielectric, such as a polyimide dielectric, which may in some cases also be coated or otherwise treated to make the droplet-operations surface hydrophobic. When the substrate includes a PCB, the following materials are examples of suitable materials: MITSUI™ BN-300 (available from MITSUI Chemicals America, Inc., San Jose Calif.); ARLON™ 11N (available from Arlon, Inc, Santa Ana, Calif.).; NELCO® N4000-6 and N5000-30/32 (available from Park Electrochemical Corp., Melville, N.Y.); ISOLA™ FR406 (available from Isola Group, Chandler, Ariz.), especially IS620; fluoropolymer family (suitable for fluorescence detection since it has low background fluorescence); polyimide family; polyester; polyethylene naphthalate; polycarbonate; polyetheretherketone; liquid crystal polymer; cyclo-olefin copolymer (COC); cyclo-olefin polymer (COP); aramid; THERMOUNT® nonwoven aramid reinforcement (available from DuPont, Wilmington, Del.); NOMEX® brand fiber (available from DuPont, Wilmington, Del.); and paper. Various materials are also suitable for use as the dielectric component of the substrate. Examples include: vapor deposited dielectric, such as PARYLENE™ C (especially on glass), PARYLENE™ N, and PARYLENE™ HT (for high temperature, ~300° C.) (available from Parylene Coating Services, Inc., Katy, Tex.); TEFLON® AF coatings; cytop; soldermasks, such as liquid photoimageable soldermasks (e.g., on PCB) like TAIYO™ PSR4000 series, TAIYO™ PSR and AUS series (available from Taiyo America, Inc. Carson City, Nev.) (good thermal characteristics for applications involving thermal control), and PROBIMER™ 8165 (good thermal characteristics for applications involving thermal control (available from Huntsman Advanced Materials Americas Inc., Los Angeles, Calif.); dry film soldermask, such as those in the VACREL® dry film soldermask line (available from DuPont, Wilmington, Del.); film dielectrics, such as polyimide film (e.g., KAPTON® polyimide film, available from DuPont, Wilmington, Del.), polyethylene, and fluoropolymers (e.g., FEP), polytetrafluoroethylene; polyester; polyethylene naphthalate; cyclo-olefin copolymer (COC); cyclo-olefin polymer (COP); any other PCB substrate material listed above; black matrix resin; polypropylene; and black flexible circuit materials, such as DuPont™ Pyralux® HXC and DuPont™ Kapton® MBC (available from DuPont, Wilmington, Del.).

Droplet transport voltage and frequency may be selected for performance with reagents used in specific assay protocols. Design parameters may be varied, e.g., number and placement of on-actuator reservoirs, number of independent electrode connections, size (volume) of different reservoirs, placement of magnets/bead washing zones, electrode size, inter-electrode pitch, and gap height (between top and bottom substrates) may be varied for use with specific reagents, protocols, droplet volumes, etc. In some cases, a substrate of the present disclosure may be derivatized with low surface-energy materials or chemistries, e.g., using deposition or in situ synthesis using poly- or per-fluorinated compounds in solution or polymerizable monomers. Examples include TEFLON® AF coatings and FLUOROPEL® coatings for dip or spray coating, other fluorinated monomers for plasma-enhanced chemical vapor deposition (PECVD), and organosiloxane (e.g., SiOC) for PECVD. Additionally, in some cases, some portion or all of the droplet-operations surface may be coated with a substance for reducing background noise, such as background fluorescence from a PCB substrate. For example, the noise-reducing coating may include a black matrix resin, such as the black matrix resins available from Toray industries, Inc., Japan.

Reagents may be provided on the droplet actuator in the droplet-operations gap or in a reservoir fluidly coupled to the droplet-operations gap. The reagents may be in liquid form, e.g., droplets, or they may be provided in a reconstitutable form in the droplet-operations gap or in a reservoir fluidly coupled to the droplet-operations gap. Reconstitutable reagents may typically be combined with liquids for reconstitution. An example of reconstitutable reagents suitable for use with the methods and apparatus set forth herein includes those described in Meathrel et al., U.S. Pat. No. 7,727,466, entitled "Disintegratable Films for Diagnostic Devices," issued on Jun. 1, 2010, the entire disclosure of which is incorporated herein by reference.

As used herein, the term "activate" when used with reference to one or more electrodes, means affecting a change in the electrical state of the one or more electrodes which, in the presence of a droplet, may result in a droplet operation. Activation of an electrode can be accomplished using alternating current (AC) or direct current (DC). Any suitable voltage may be used. For example, an electrode may be activated using a voltage which is greater than about 150 V, or greater than about 200 V, or greater than about 250 V, or from about 275 V to about 1000 V, or about 300 V. Where an AC signal is used, any suitable frequency may be employed. For example, an electrode may be activated using an AC signal having a frequency from about 1 Hz to about 10 MHz, or from about 10 Hz to about 60 Hz, or from about 20 Hz to about 40 Hz, or about 30 Hz. Electrodes of a droplet actuator may be controlled by a controller or a processor, which may be provided as part of an assay system. The controller or processor may include processing functions as well as data and software storage and input and output capabilities.

As used herein, a "droplet operation" includes any manipulation of a droplet on or within a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations that are sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to volume of the resulting droplets (i.e., the volume of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading.

Droplet operations may be electrode-mediated. In some cases, droplet operations are further facilitated by the use of hydrophilic and/or hydrophobic regions on surfaces and/or by physical obstacles. For examples of droplet operations, see the patents and patent applications cited above under the definition of "droplet actuator."

Impedance or capacitance sensing or imaging techniques may sometimes be used to determine or confirm the outcome of a droplet operation or to determine or confirm a volume or level of liquid within a receiving cavity or well. Examples of such techniques are described in Sturmer et al., International Patent Pub. No. WO/2008/101194, entitled "Capacitance Detection in a Droplet Actuator," published on Dec. 30, 2009, the entire disclosure of which is incorporated herein by reference. Generally speaking, the sensing or imaging techniques may be used to confirm the presence or absence of a droplet at a specific electrode or within a well or receiving cavity. For example, the presence of a dispensed droplet at the destination electrode following a droplet dispensing operation confirms that the droplet dispensing operation was effective. Similarly, the presence of a droplet at a detection spot at an appropriate step in an assay protocol may confirm that a previous set of droplet operations has successfully produced a droplet for detection.

Droplet transport time can be quite fast. For example, in various embodiments, transport of a droplet from one electrode to the next may exceed about 1 sec, or about 0.1 sec, or about 0.01 sec, or about 0.001 sec. In one embodiment, the electrode is operated in AC mode but is switched to DC mode for imaging. It is helpful for conducting droplet operations for the footprint area of droplet to be similar to electrowetting area; in other words, 1x-, 2x- 3x-droplets are usefully controlled operated using 1, 2, and 3 electrodes, respectively. If the droplet footprint is greater than number of electrodes available for conducting a droplet operation at a given time, the difference between the droplet size and the number of electrodes should typically not be greater than 1; in other words, a 2x droplet is usefully controlled using 1 electrode and a 3x droplet is usefully controlled using 2 electrodes. When droplets include beads, it is useful for droplet size to be equal to the number of electrodes controlling the droplet, e.g., transporting the droplet.

As used herein, a "filler liquid" includes a liquid associated with a droplet-operations substrate of a droplet actuator, which liquid is sufficiently immiscible with a droplet phase to render the droplet phase subject to electrode-mediated droplet operations. For example, the droplet-operations gap of a droplet actuator is typically filled with a filler liquid. The filler liquid may be a non-polar liquid. The filler liquid may, for example, be or include a low-viscosity oil, such as silicone oil or hexadecane filler liquid. The filler liquid may be or include a halogenated oil, such as a fluorinated or perfluorinated oil. The filler liquid may fill the entire gap of the droplet actuator or may coat one or more surfaces of the droplet actuator. Filler liquids may be conductive or nonconductive. Filler liquids may be selected to improve droplet operations and/or reduce loss of reagent or target substances from droplets, improve formation of microdroplets, reduce cross contamination between droplets, reduce contamination of droplet actuator surfaces, reduce degradation of droplet actuator materials, etc. For example, filler liquids may be selected for compatibility with droplet actuator materials. As an example, fluorinated filler liquids may be usefully employed with fluorinated surface coatings. Fluorinated filler liquids are useful to reduce loss of lipophilic compounds, such as umbelliferone substrates like 6-hexadecanoylamido-4-methylumbelliferone substrates (e.g., for use in Krabbe, Niemann-Pick, or other assays); other umbelliferone substrates are described in Winger et al., U.S. Patent Pub. No. 20110118132, entitled "Enzymatic Assays Using Umbelliferone Substrates with Cyclodextrins in Droplets of Oil," published on May 19, 2011, the entire disclosure of which is incorporated herein by reference. Examples of suitable fluorinated oils include those in the Galden line, such as Galden HT170 (bp=170° C., viscosity=1.8 cSt, density=1.77), Galden HT200 (bp=200 C, viscosity=2.4 cSt, d=1.79), Galden HT230 (bp=230 C, viscosity=4.4 cSt, d=1.82) (all from Solvay Solexis); those in the Novec line, such as Novec 7500 (bp=128 C, viscosity=0.8 cSt, d=1.61), Fluorinert FC-40 (bp=155° C., viscosity=1.8 cSt, d=1.85), Fluorinert FC-43 (bp=174° C., viscosity=2.5 cSt, d=1.86) (both from 3M). In general, selection of perfluorinated filler liquids is based on kinematic viscosity (<7 cSt, but not required), and on boiling point (>150° C., but not required, for use in DNA/RNA-based applications (PCR, etc.)). Filler liquids may, for example, be doped with surfactants or other additives. For example, additives may be selected to improve droplet operations and/or reduce loss of reagent or target substances from droplets, formation of microdroplets, cross contamination between droplets, contamination of droplet actuator surfaces, degradation of droplet actuator materials, etc. Composition of the filler liquid, including surfactant doping, may be selected for performance with reagents used in the specific assay protocols and effective interaction or non-interaction with droplet actuator materials. Examples of filler liquids and filler liquid formulations suitable for use with the methods and apparatus set forth herein are provided in Srinivasan et al, International Patent Pub. No. WO/2010/027894, entitled "Droplet Actuators, Modified Fluids and Methods," published on Jun. 3, 2010; Srinivasan et al, International Patent Pub. No. WO/2009/021173, entitled "Use of Additives for Enhancing Droplet Operations," published on Feb. 12, 2009; Sista et al., International Patent Pub. No. WO/2008/098236, entitled "Droplet Actuator Devices and Methods Employing Magnetic Beads," published on Jan. 15, 2009; and Monroe et al., U.S. Patent Pub. No. 20080283414, entitled "Electrowetting Devices," published on Nov. 20, 2008, the entire disclosures of which are incorporated herein by reference, as well as the other patents and patent applications cited herein. Fluorinated oils may in some cases be doped with fluorinated surfactants, e.g., Zonyl FSO-100 (Sigma-Aldrich) and/or others. A filler liquid is typically a liquid. In some embodiments, a filler gas can be used instead of a liquid. Exemplary filler liquids are described in U.S. Patent Publication No. 2014/0231259, which is incorporated herein by reference in its entirety.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface. In one example, filler liquid can be considered as a film between such liquid and the electrode/array/matrix/surface.

When a droplet is described as being "on" or "loaded on" a droplet actuator, it should be understood that the droplet is arranged on or within the droplet actuator in a manner which facilitates using the droplet actuator to conduct one or more droplet operations or in a manner which facilitates sensing of a property of or a signal from the droplet.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

Figure 1:
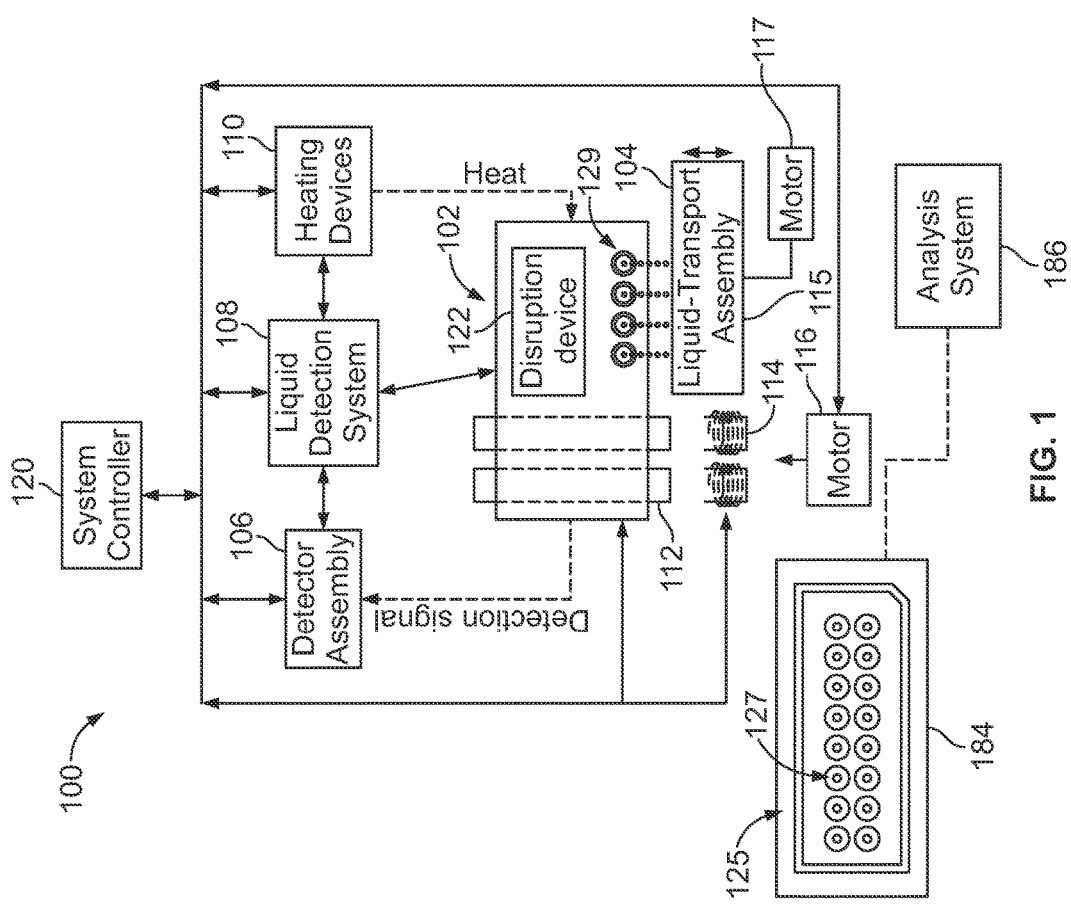
FIG. 1 is a block diagram of an assay system configured to conduct designated reactions formed in accordance with an embodiment.

FIG. 1 is a block diagram of an assay system 100 configured to conduct designated reactions formed in accordance with an embodiment while utilizing immiscible liquids. The assay system 100 includes a fluidic system 102 that is operably positioned with respect to or operably coupled to a liquid-transport assembly 104, a detector assembly 106, a liquid-detection system 108, and one or more heating devices 110. The assay system 100 may also include a phase-separation device 125, a flow-facilitating device 184, and an analysis system 186. In some embodiments, the fluidic system 102 may be referred to as a sample preparation system. The fluidic system 102 may be a droplet actuator, such as a DF device or cartridge, that is configured to utilize DF technology to conduct droplet operations on discrete droplets. Fluidic systems may also include MEMS, LOC, and/or POC devices. It is noted that the terms DF device, flow cell, MEMS device, LOC device, and POC device are not necessarily mutually exclusive. For example, a single fluidic system may be characterized as a MEMS device, a LOC device, and/or a POC device.

In certain embodiments, the fluidic system 102 is a droplet actuator that includes a first substrate and a second substrate that are separated by a droplet-operations gap (not shown). The droplet-operations gap may define an interior cavity where the droplets are located during operation of the fluidic system 102. The first substrate may include an arrangement of electrically addressable electrodes. In some cases, the second substrate may include a reference electrode plane made, for example, from conductive ink or indium tin oxide (ITO). The first substrate and the second substrate may be coated with a hydrophobic material. Droplet operations are conducted in the droplet-operations gap. The space around the droplets (i.e., the droplet-operations gap between first and second substrates) may be filled with a filler liquid that is immiscible with respect to the droplets. For example, the filler liquid may be an inert fluid, such as silicone oil, that prevents evaporation of the droplets and is used to facilitate their transport within the device. In some cases, droplet operations may be effected by varying the patterns of voltage activation. Droplet operations may include merging, splitting, mixing, and dispensing of droplets.

The fluidic system 102 may be designed to fit onto or within a system housing (not shown) of the assay system 100. The system housing may hold the fluidic system 102 and house other components of the assay system, such as, but not limited to, the liquid-transport assembly 104, the detector assembly 106, the liquid-detection system 108, and one or more heating devices 110. For example, the system housing may house one or more magnets 112, which may be permanent magnets. Optionally, the system housing may house one or more electromagnets 114. The magnets 112 and/or electromagnets 114 may be positioned in relation to the fluidic system 102 for immobilization of magnetically responsive substrate beads. Optionally, the positions of the magnets 112 and/or the electromagnets 114 may be controlled by a magnet-locating motor 116. Additionally, the system housing may house one or more of the heating devices 110 for controlling the temperature within, for example, certain reaction and/or washing zones of the fluidic system 102. In one example, the heating devices 110 may be heater bars that are positioned in relation to the fluidic system 102 for providing thermal control thereof.

The assay system 100 may include a system controller 120 that communicates with the various components of the assay system 100 for automatically controlling the assay system 100 during one or more protocols. For example, the system controller 120 may be communicatively coupled to the fluidic system 102, the electromagnets 114, the magnet-locating motor 116, the heating devices 110, the detector assembly 106, the liquid-detection system 108, and the liquid-transport assembly 104. The system controller 120 may also be communicatively coupled to a user interface (not shown) that is configured to receive user inputs for operating the assay system 100.

The system controller 120 may include one or more logic-based devices, including one or more microcontrollers, processors, reduced instruction set computers (RISC), application specific integrated circuits (ASICs), field programmable gate array (FPGAs), logic circuits, and any other circuitry capable of executing functions described herein. In an exemplary embodiment, the system controller 120 executes a set of instructions that are stored in one or more storage elements in order to perform one or more protocols. Storage elements may be in the form of information sources or physical memory elements within the assay system 100. The protocols performed by the assay system 100 may be to carry out, for example, quantitative analysis of DNA or RNA, protein analysis, DNA sequencing (e.g., sequencing-by-synthesis (SBS)), sample preparation, and/or preparation of fragment libraries for sequencing. For embodiments that utilize a droplet actuator, the system controller 120 may control droplet manipulation by activating/deactivating electrodes to perform one or more of the protocols. The system controller 120 may also control operation and positioning of the liquid-transport assembly 104 as described herein.

The set of instructions may include various commands that instruct the assay system 100 to perform specific operations such as the methods and processes of the various embodiments described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, or a program module within a larger program or a portion of a program module. The software also may include modular programming in the form of object-oriented programming. After obtaining the detection data, the detection data may be automatically processed by the assay system 100, processed in response to user inputs, or processed in response to a request made by another processing machine (e.g., a remote request through a communication link).

The system controller 120 may be connected to the other components or sub-systems of the assay system 100 via communication links, which may be hardwired or wireless. The system controller 120 may also be communicatively connected to off-site systems or servers. The system controller 120 may receive user inputs or commands, from a user interface (not shown). The user interface may include a keyboard, mouse, a touch-screen panel, and/or a voice recognition system, and the like.

The system controller 120 may serve to provide processing capabilities, such as storing, interpreting, and/or executing software instructions, as well as controlling the overall operation of the assay system 100. The system controller 120 may be configured and programmed to control data and/or power aspects of the various components. Although the system controller 120 is represented as a single structure in FIG. 1, it is understood that the system controller 120 may include multiple separate components (e.g., processors) that are distributed throughout the assay system 100 at different locations. In some embodiments, one or more components may be integrated with a base instrument and one or more components may be located remotely with respect to the instrument.

In some embodiments, the detector assembly 106 is an imaging system that is positioned in relation to the fluidic system 102 to detect light signals (e.g., absorbance, reflection/refraction, or light emissions) from the fluidic system 102. The imaging system may include one or more light sources (e.g., light-emitting diodes (LEDs) and a detection device, such as a charge-coupled device (CCD) camera or complementary-metal-oxide semiconductor (CMOS) imager. In some embodiments, the detector assembly 106 may detect light signals that are emitted from chemiluminescence. Yet still in other embodiments, the detector assembly 106 may not be an imaging system. For example, the detector assembly 106 may be one or more electrodes that detect an electrical property of a liquid.

The liquid-detection system 108 may be configured to detect a location of a liquid and/or a volume of the liquid. For instance, the liquid-detection system 108 may be configured to identify a location of a droplet within the fluidic system 102 and/or a volume of a droplet within the fluidic system 102 or of a liquid within a reservoir (or receiving cavity). In certain embodiments, the liquid-detection system 108 may include circuitry for detecting impedance within a droplet or reservoir. For example, the liquid-detection system 108 may include electrodes that form an impedance spectrometer. The liquid-detection system 108 may be used to monitor the capacitive loading of any electrode, such as any droplet-operations electrode, with or without a droplet thereon. For examples of suitable capacitance detection techniques, see Sturmer et al., International Patent Publication No. WO/2008/101194, entitled "Capacitance Detection in a Droplet Actuator," published on Aug. 21, 2008; and Kale et al., International Patent Publication No. WO/2002/080822, entitled "System and Method for Dispensing Liquids," published on Oct. 17, 2002; the entire disclosures of which are incorporated herein by reference. Alternatively, other devices or elements may be used to detect a location and/or volume of the liquid within the fluidic system 102.

For instance, the detector assembly 106 may detect light signals that propagate through and/or are emitted from a designated region. Based on the light signals, the liquid-detection system 108 may confirm whether a droplet is located at the designated region and/or determine that a liquid has an approximate volume at the designated region. The liquid-detection system 108 may include probes that detect a level of the liquid.

Optionally, the fluidic system 102 may include a disruption device 122. The disruption device 122 may include any device that promotes disruption (lysis) of materials, such as tissues, cells and spores in a droplet actuator. The disruption device 122 may, for example, be a sonication mechanism, a heating mechanism, a mechanical shearing mechanism, a bead beating mechanism, physical features incorporated into the fluidic system 102, an electric field generating mechanism, a thermal cycling mechanism, and any combinations thereof. The disruption device 122 may be controlled by the system controller 120.

The liquid-transport assembly 104 may include a storage housing 115 and a transport motor 117. The storage housing 115 includes a reservoir or cavity that is configured to store liquids (e.g., reagents, buffer solutions, filler liquid, etc.) that are used to conduct the designated reactions. The transport motor 117 is configured to move the storage housing 115 relative to the fluidic system 102 to load liquids into and/or remove liquids from the fluidic system 102. The liquids may be loaded into or drawn through access ports 129 that provide access to an interior cavity of the fluidic system 102. By way of example only, the transport motor 117 (and the magnet-locating motor 116) may include one or more direct drive motors, direct current (DC) motors, solenoid drivers, linear actuators, piezoelectric motors, and the like.

The phase-separation device 125 has a plurality of receiving cavities 127 that are each configured to receive a liquid mixture from the fluidic system 102. The liquid mixtures may be automatically transferred through the liquid-transport assembly 104 or may be manually transferred by a user (e.g., technician). In particular embodiments, the liquid mixture may include a polar liquid (e.g., an aqueous solution including a biological sample) and a non-polar liquid (e.g., silicone oil). The phase-separation device 125 may be configured to separate the polar liquid from the non-polar liquid by significantly reducing a volume of the non-polar liquid. For example, the phase-separation device 125 may absorb the non-polar liquid into a body of the phase-separation device 125 while holding the polar liquid within the receiving cavities. In an exemplary embodiment, the liquid mixture may be withdrawn manually from the fluidic system 102. For instance, a user may insert one or more nozzles of a pipettor (or multi-pipettor) through the access ports 129 and remove the liquid mixture from the fluidic system 102. In other embodiments, the liquid mixture may be automatically removed using, for examples, pipettors or tubes fluidically controlled by an automated machine. Alternatively, the assay system 100 may include one or more fluidic channels that are in flow communication with the receiving cavities 127 and a pump system (not shown) that induces a flow of the liquid mixture into the receiving cavities 127.

In some embodiments, the liquid mixture is separated in a passive manner. For example, the liquid mixture may rest on top of a porous membrane of the phase-separation device and gravity may cause one or more liquids to flow into the porous membrane while impeding the flow of another liquid (s) into the porous membrane. In other embodiments, the assay system 100 includes the flow-facilitating device 184. The flow-facilitating device 184 may be, for example, a system that is configured to hold and move the phase-separation device 125. By way of example, the flow-facilitating device 184 may agitate or shake the phase-separation device 125 or cause vibrations within the phase-separation device 125 to move the liquid mixture and facilitate separating the liquid mixture. As another example, the flow-facilitating device 184 may be a centrifuge that receives the phase-separation device 125 and rotates to facilitate separating the liquid mixture.

After effectively isolating one or more liquids, the isolated liquids may be provided to an analysis system 186 for further preparation and/or analysis. For example, the isolated liquids may be provided to a system for conducting PCR and/or sequencing nucleic acids that are derived from the isolated liquids. However, embodiments set forth herein are not limited to sequencing protocols and other assay protocols may be implemented.

Analysis systems that may be capable of carrying out one or more of the SBS protocols described above include systems developed by Illumina, Inc., such as the MiSeq, HiSeq 2500, HiSeq X Ten, and HiScan systems. Systems capable of carrying out one or more of the SBS protocols described above are described in U.S. application Ser. Nos. 13/273,666 and 13/905,633; WO 07/123744; U.S. Pat App. Pub. Nos. 2012/0270305 A1; 2013/0023422 A1; and 2013/0260372 A1; and U.S. Pat. Nos. 5,528,050; 5,719,391; 8,158,926 and 8,241,573, each of which is incorporated herein by reference in its entirety.

It will be appreciated that one or more aspects of the embodiments set forth herein may be embodied as a method, system, computer readable medium, and/or computer program product. The term "system" is to be interpreted broadly and may mean any assembly or device. Aspects may take the form of hardware embodiments, software embodiments (including firmware, resident software, micro-code, etc.), or embodiments combining software and hardware aspects that may all generally be referred to herein as a "circuit," "module" or "system." Furthermore, the methods may take the form of a computer program product on a computer-usable storage medium having computer-usable program code embodied in the medium.

FIG. 2 is illustrates a plan view of a droplet actuator 130, which may be used as the fluidic system within an assay system, such as the assay system 100 (FIG. 1). The droplet actuator 130 includes a bottom substrate 132 and a top substrate 134 that is positioned over the bottom substrate 132. The bottom substrate 132 may include, for example, a printed circuit board (PCB) having an array of electrodes thereon for conducting droplet operations. The top substrate 134 may be a cover plate that is mounted over the bottom substrate 132. The top substrate 134 includes an array of access ports 136. For example, in the illustrated embodiment, the access ports 136 include a filler inlet 138, rows of reagent inlets 140, 142, a row of adaptor inlets 144, a row of sample inlets 146, and a row of liquid-mixture outlets 148. Each of the access ports 136 provides fluidic access to an interior cavity (or droplets-operation gap) that is located between the top and bottom substrates 134, 132. The droplet actuator 130 may receive liquids (e.g., one or more reagents, buffer solutions, filler liquid, and the like) through the access ports 136 and/or may have liquids withdrawn through the access ports 136, such as the liquid-mixture outlets 148.

Figure 3:
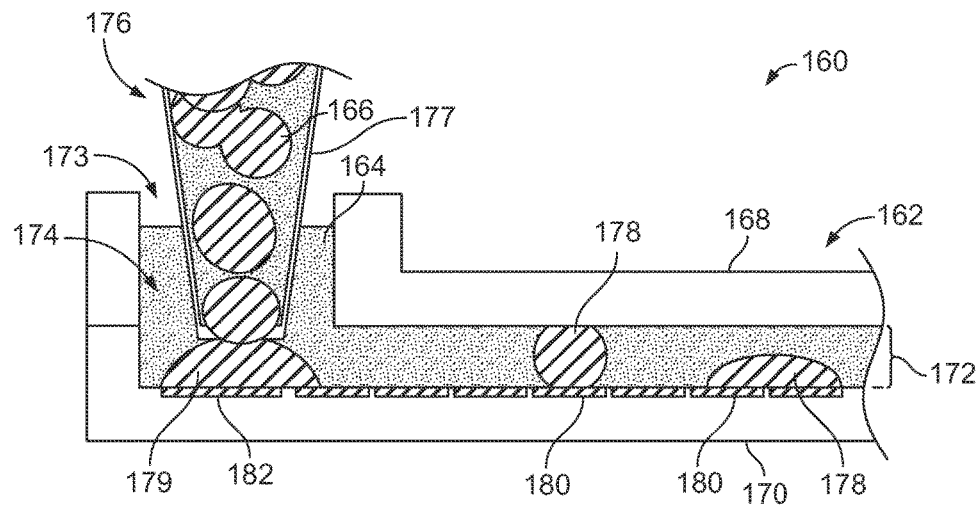
FIG. 3 illustrates a schematic side view of a fluidic system formed in accordance with an embodiment.

FIG. 3 illustrates a schematic cross-section of a portion of a fluidic system 160 formed in accordance with an embodiment. The fluidic system 160 may be or include a DF device or droplet actuator, such as the droplet actuator 130 (FIG. 2). The fluidic system 160 has a housing 162 that is configured to hold a filler liquid 164 (e.g., oil) and one or more solutions 166 (e.g., reagent or sample solutions). The housing 162 may be formed from multiple components. For example, the housing 162 includes a top or cover substrate 168 and a bottom substrate 170. The top substrate 168 is mounted to the bottom substrate 170. The top and bottom substrates 168, 170 are separated by an operational gap (or droplets-operation gap) that defines a device channel 172. The top substrate 168 has an access opening 173.

When the top substrate 168 is mounted to the bottom substrate 170, the top and bottom substrates 168, 170 form a removal cavity 174 that is accessible through the access opening 173 and in fluid communication with the device channel 172. The removal cavity 174 is sized and shaped to hold the solution 166 and allow an instrument 176 to draw liquid from the removal cavity 174. The drawn liquid may include both the solution 166 and the filler liquid 164 and be referred to as a liquid mixture. The instrument 176 is illustrated as having a nozzle 177 that is inserted through the access opening 173. The instrument 176 may be, for example, a pipettor or a multi-pipettor (also referred to as a multi-channel pipette). In other embodiments, the instrument 176 may include a flexible tube that is held within the removal cavity 174. However, it should be understood that other mechanisms for removing a designated volume of the liquid mixture may be used.

In the illustrated embodiment, droplets 178 may be transported through the device channel 172 to accumulate and form a larger droplet or volume 179 within the removal cavity 174. The larger droplet 179 may be formed from multiple droplets 178 having the same composition or multiple droplets 178 in which at least two of the droplets have different compositions. In alternative embodiments, each single droplet 178 is separately removed from the removal cavity 174 prior to the next droplet 178 being located over the reservoir electrode 182. To transport the droplets 178, the fluidic system 160 may include an arrangement of electrodes 180 that are positioned along the device channel 172. For instance, the bottom substrate 170 includes a series of the electrodes 180 positioned along the device channel 172. The top substrate 168 may include a reference electrode (not shown). Alternatively, the bottom substrate 170 may include a reference electrode. The bottom substrate 170 may also include a reservoir electrode 182. The reservoir electrode 182 may be utilized by the system controller to hold a larger volume of the solution 166. For example, in the illustrated embodiment, the electrode 182 is sized and shaped to have a larger area than the electrodes 180. The electrodes 180, 182 are electrically coupled to a system controller (not shown), such as the system controller 120 (FIG. 1). The system controller is configured to control voltages of the electrodes 180, 182 to conduct electrowetting operations. More specifically, the electrodes 180, 182 may be activated/deactivated to conduct designated reactions and then transport droplets 178 toward the removal cavity 174 through the device channel 172.

Alternatively or in addition to holding the larger droplet 179, the reservoir electrode 182 may be utilized to detect a volume of the larger droplet 179. More specifically, the electrode 182 may communicate information that may be used to determine that a designated volume of the solution 166 exists above the electrode 182. If the volume is determined to be sufficient, the system controller may activate a mechanism that is configured to induce flow of the liquid within the removal cavity 174 through the nozzle 177. More specifically, the mechanism may draw at least a portion of the solution 166 and the filler liquid 164. The amount of liquid removed may be a predetermined or predefined approximate amount. For example, a pipettor may be configured to remove a substantially common amount of liquid with each pump or stroke of the pipettor.

Figure 4:
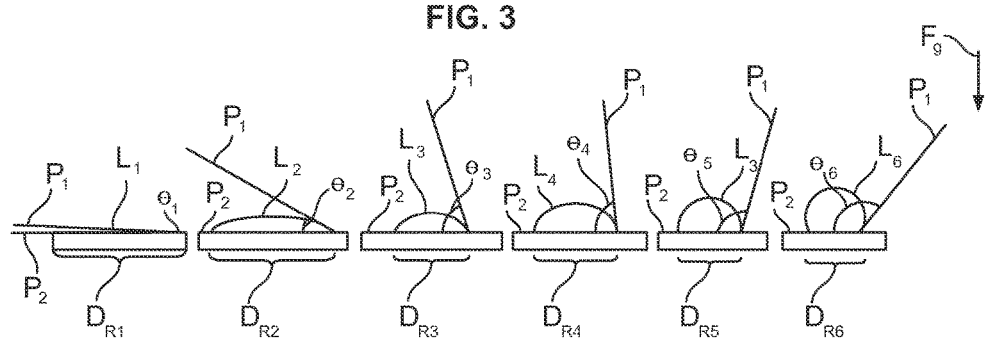
FIG. 4 illustrates a series of drops of liquid on respective surfaces.

FIG. 4 illustrates a series of droplets of liquid $L_1$-$L_6$ on respective solid surfaces. As discussed above, embodiments described herein utilize the forces experienced by a liquid to control flow of the liquid through a porous membrane and/or a shape of the liquid within a receiving cavity. These forces include cohesive forces (i.e., attractive forces between like molecules of the liquid) and adhesive forces (i.e., attractive forces between molecules of the liquid and the solid surface that contacts the liquid or vapor that surrounds the liquid). Cohesive and adhesive forces arise from the interaction of atoms and molecules that are located along, for example, a liquid-vapor interface and a liquid-solid interface. Another force that affects liquid in certain embodiments is gravity or the gravitational force $F_g$.

FIG. 4 shows resting diameters $D_{R1}$-$D_{R6}$ and contact angles $\theta_1$-$\theta_6$ for droplets of the liquids $L_1$-$L_6$. A resting diameter $D_R$ is a diameter of the droplet of a liquid on a corresponding planar solid surface in which the droplet of the liquid is not compressed or contained by walls. The resting diameter $D_R$ is measured parallel to the planar solid surface. A contact angle $\theta$ is the angle formed by the intersection of two planes ($P_1$ and $P_2$) tangent to the liquid L and the corresponding solid surface. When the contact angle $\theta$ is greater than 90°, the resting diameter $D_R$ remains substantially the same (e.g., $D_{R5}$ and $D_{R6}$ are about equal). The contact angle $\theta$ indicates a wetting ability of the liquid to the surface. Wetting is a liquid's ability to spread along a solid surface. The wetting of a solid surface by a liquid is controlled by the intermolecular interactions of molecules along an interface between the two phases. If the adhesive forces are relatively greater than the cohesive forces, the wetting of the liquid to the surface is greater (i.e., the contact angle $\theta$ will be small as shown with contact angles $\theta_1$ and $\theta_2$ in FIG. 1). If the cohesive forces are relatively greater than the adhesive forces, the wetting of the liquid to the surface is smaller (i.e., the contact angle $\theta$ will be large as shown with contact angles $\theta_5$ and $\theta_6$).

Surface tension in a liquid is caused by the cohesive forces of the liquid and can have an affect on the contact angle $\theta$. For instance, as the surface tension increases, an ability of the liquid to reduce its contact area (i.e., bead up) along the solid surface increases. Surfaces of solids, however, may be characterized as having a surface energy. As the surface energy of a solid increases, the ability of the solid to interact with the liquid also increases (i.e., the contact angle $\theta$ decreases). As an example, when a liquid of low surface tension is placed on a solid of high surface energy, the liquid spreads across the surface and has a small contact angle $\theta$, such as shown with respect to the liquids $L_1$ and $L_2$. If a liquid has a high surface tension and is placed on a surface of low surface energy, the liquid may form a bead on the surface and have a high contact angle $\theta$, such as shown with respect to the liquids $L_5$ and $L_6$. As described herein, flow of a liquid through a porous membrane and/or a shape of the liquid within a receiving cavity may be determined by the surface tension of the liquid and the surface energy of the porous membrane.

The interaction between a polar liquid and the solid surface can be characterized as hydrophobic or hydrophilic. As used herein, a solid surface is hydrophobic if it repels an aqueous or polar liquid. For example, the contact angle $\theta$ between the aqueous or polar liquid L and the hydrophobic surface of the solid is typically greater than 75 degrees or 85 degrees. A surface is hydrophilic if it is attracted to an aqueous or polar liquid. For example, the contact angle $\theta$ between the aqueous or polar liquid and the hydrophilic surface of the solid will typically be less than 75 degrees.

A non-polar liquid, such as alkanes, oils, and fats may form part of a liquid mixture. Non-polar liquids may be attracted to a surface that has a hydrophobic interaction with aqueous or polar liquids. Likewise, non-polar liquids are not attracted to a surface that has a hydrophilic interaction with aqueous or polar liquids. In particular embodiments, hydrophobic surfaces may be used to permit flow of a non-polar liquid into a porous membrane.

Embodiments described herein utilize the contact angle or the wetting of a liquid and a shape of a solid surface to control flow of the liquid (e.g., non-polar liquid) through a porous membrane and/or a shape of a liquid (e.g., polar liquid) within a receiving cavity. Other factors may affect the contact angle $\theta$ or the wetting of a liquid to a solid. For example, a purity of the liquid or whether a surfactant is used may affect the surface tension of the liquid and the molecular interactions along the solid-liquid interface. A purity of the solid or whether a coating is placed on the solid surface may affect the surface energy of a solid. Also, temperature of the environment, a composition of the surrounding air, and the roughness or smoothness of the surface may all affect the interactions between the liquid L and the solid surface.

Figure 5:
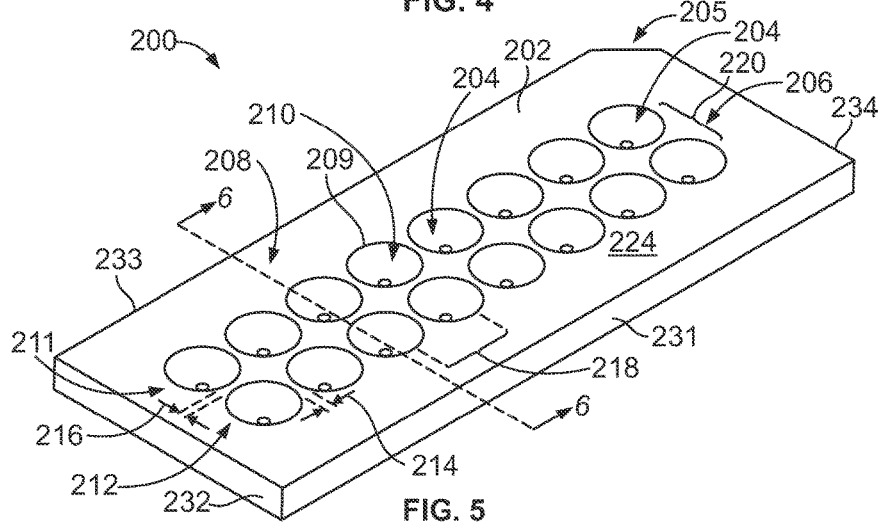
FIG. 5 is a perspective view of a phase-separation device in accordance with an embodiment.

FIG. 5 is a perspective view of a phase-separation device 200. The phase-separation device 200 may be similar or identical to the phase-separation device 125 (FIG. 1). The phase-separation device 200 includes a support frame 202 and multiple receiving cavities 204 that are coupled to the support frame 202. Each of the receiving cavities 204 is sized and shaped to receive a designated amount of a liquid mixture. The support frame 202 extends between and joins the receiving cavities 204. The support frame 202 may hold the receiving cavities 204 in fixed positions with respect to one another.

The receiving cavities 204 may be positioned in a designated or predetermined array 206. As shown, the array 206 is a two-dimensional array, but the array 206 may be one dimensional in other embodiments. It is also contemplated that the array 206 may be a three-dimensional array in other embodiments. For example, the phase-separation device 200 may be shaped such that the receiving cavities are located at different heights or elevations (e.g., first row at one step or level, second row at a different step or level). The number and positions of the receiving cavities 204 in the array 206 may be based on a designated protocol that utilizes the phase-separation device 200. For example, the array 206 includes two rows 211, 212 of receiving cavities 204 in which each row has a series of eight receiving cavities 204. The number of receiving cavities 204 may be based on the number of different liquid mixtures that are withdrawn from a fluidic system (not shown). The positions of the receiving cavities 204 may facilitate depositing the liquid mixtures into the receiving cavities 204. For instance, the positions of the receiving cavities 204 relative to one another may be based on positions of nozzles held by a multi-pipettor so that the liquid mixtures may be simultaneously deposited into a plurality of receiving cavities 204 and/or may be simultaneously withdrawn.

The phase-separation device 200 includes an operating or active side 208 that is configured to face or be accessible to a user of the phase-separation device 200. The receiving cavities 204 have respective cavity edges 209 that define access openings 210 of the receiving cavities 204. The receiving cavities 204 open to the operating side 208.

Adjacent receiving cavities 204 in the same row may be separated by a cavity gap 214, and adjacent receiving cavities 204 in different rows may be separated by a cavity gap 216. Likewise, each row of receiving cavities 204 may have a center-to-center spacing 218. Adjacent receiving cavities 204 in different rows may have a center-to-center spacing 220. The cavity gaps 214, 216 and center-to-center spacings 218, 220 may be based on an intended use or application of the phase-separation device 200. In some embodiments, the cavity gaps 214, 216 and center-to-center spacings 218, 220 are based on a contour or shape of the receiving cavity 204.

In the illustrated embodiment, the support frame 202 is a substantially two-dimensional structure. For example, the support frame 202 may be panel-shaped or board-shaped. The operating side 208 has a side surface 224 that is substantially planar, except for the receiving cavities 204. In other embodiments, the side surface 224 may not be planar. For example, the support frame 202 may include a plurality of bridges or links that extend between and join the receiving cavities 204.

The phase-separation device 200 may have body edges 231-234 that define a profile of the phase-separation device 200. As shown, the profile is substantially rectangular and includes a keying feature 205. The keying feature 205 may visually indicate to a user the orientation of the phase-separation device 200. Alternatively, the phase-separation device 200 may be positioned within a seating space or holder. In such embodiments, the keying feature 205 may ensure that the phase-separation device 200 has the proper orientation within the seating space. Although the keying feature 205 is illustrated as a chamfered corner in FIG. 5, the keying feature 205 may have other shapes in other embodiments. For example, the keying feature 205 may be a projection.

Figure 6:
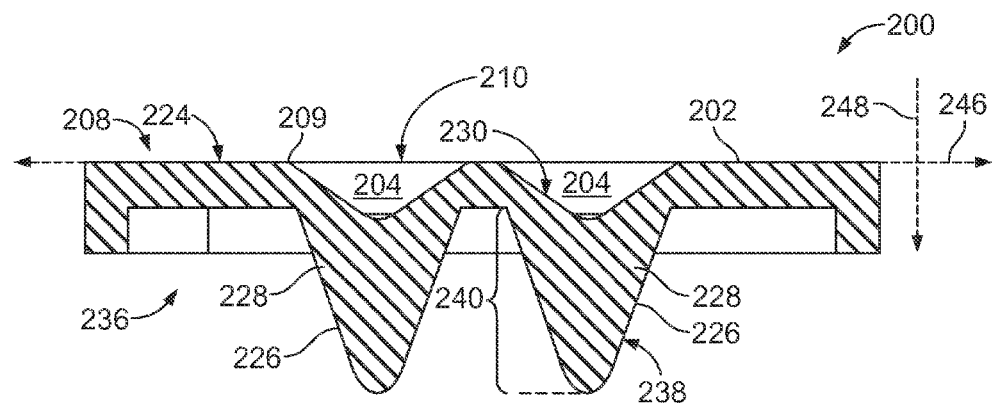
FIG. 6 is a cross-section of the phase-separation device taken along the line 6-6 in FIG. 5.

FIG. 6 is a cross-section of the phase-separation device 200 taken along the line 6-6 in FIG. 5. In some embodiments, the operating side 208 or the side surface 224 may coincide with a reference plane 246. In the illustrated embodiment, the cavity edges 209 that define corresponding access openings 210 may coincide with the reference plane 246. However, in other embodiments, the cavity edges 209 may not extend within a common plane and, for example, may have non-planar paths. In an exemplary embodiment, when the phase-separation device 200 is operably positioned for receiving a liquid mixture within the receiving cavities 204, a gravitational force axis 248 may extend normal to the reference plane 246. However, it should be understood that the phase-separation device 200 is not required to have a particular orientation with respect to gravity and may have other orientations in other embodiments. For example, the phase-separation device 200 may be tilted (e.g., 30°, 45°, etc.) with respect to the reference plane 246 shown in FIG. 6 when filtering liquids in some embodiments. It is also contemplated that the phase-separation device 200 could be rotated more extensively (e.g., 90°, 180°, etc.) in effectively closed systems.

As shown, the phase-separation device 200 may also include filter bodies 226. Each of the filter bodies 226 may include a porous membrane 228 having a filter surface 230 that defines a corresponding receiving cavity 204. The filter bodies 226 may have fixed positions with respect to each other. In an exemplary embodiment, the phase-separation device 200 includes a unitary body of the porous membrane 228. The unitary body of the porous membrane 228 may be shaped to form each of the filter bodies 226 and the support frame 202 of the phase-separation device 200. In other embodiments, however, the phase-separation device 200 may include separate components that are assembled together. For example, the support frame 202 may include links (e.g., plastic or metal) that extend between and join separate filter bodies 226 that each comprise the porous membrane 228.

The phase-separation device 200 includes a mounting side 236 that is generally opposite the operating side 208. The filter bodies 226 are positioned along the mounting side 236. Each of the filter bodies 226 has an outer surface 238. The filter bodies 226 may form corresponding absorption regions 240 that are generally defined between the outer surface 238 and the filter surface 230 of the respective filter body 226. The absorption region 240 is located adjacent to the receiving cavity 204 and may represent a space of the porous membrane 228 that absorbs a liquid from the receiving cavity 204. The absorption region 240 may be located generally below the corresponding receiving cavity 204. A thickness of a respective filter body 226 (or absorption region 240) is defined between the outer surface 238 and the filter surface 230. The thickness is not uniform in the illustrated embodiment. In some embodiments, the thickness and/or a volume of the absorption region 240 is greater than a volume of the receiving cavity 204. In other embodiments, however, the thickness and/or volume of the absorption region 240 is less than or equal to a volume of the receiving cavity 204.

In certain embodiments, the filter bodies 226 have designated shapes and are positioned relative to one another to permit the filter bodies 226 to be inserted into corresponding wells of a multi-well plate (not shown). In such embodiments, the multi-well plate may support the phase-separation device 200 and hold the phase-separation device 200 in a substantially stationary position. The wells (not shown) of the multi-well plate may also provide a space for receiving any liquid that flows entirely through the filter bodies 226 as described below.

Figure 7:
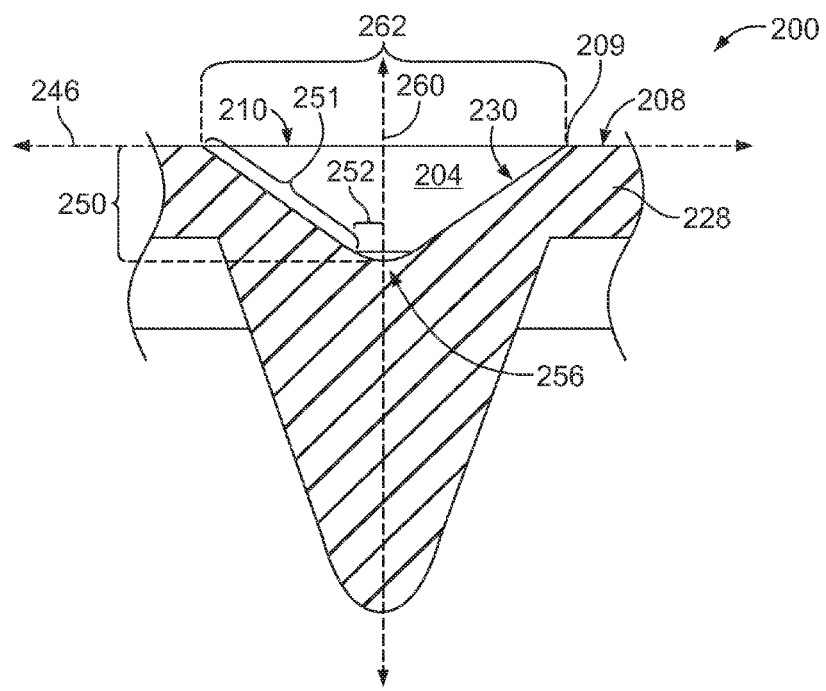
FIG. 7 is an enlarged cross-section of the phase-separation device of FIG. 5 illustrating an exemplary receiving cavity.

FIG. 7 is an enlarged cross-section of the phase-separation device 200 illustrating an exemplary receiving cavity 204 in greater detail. The receiving cavity 204 may be entirely defined by the filter surface 230 of the porous membrane 228. In other embodiments, however, the filter surface 230 may only partially define the receiving cavity 204. For example, the phase-separation device 200 may include a gasket (not shown) that is positioned on top of the operating side 208. The gasket may have openings that align with the access openings 210. Collectively, the gasket and the filter surface 230 may define the receiving cavity 204.

The porous membrane 228 may include one or more materials having pores that permit a liquid (e.g., a polar liquid or a non-polar liquid) to flow through the porous membrane 228. In the illustrated embodiment, the entire phase-separation device 200 is formed from a single unitary piece of porous membrane. As such, the same side surface 224 may be shaped to form each of the receiving cavities 204. In other embodiments, the phase-separation device 200 may be formed from multiple porous membranes that are coupled to each other. Such porous membranes may be the same type or different types (e.g., have different properties or characteristics).

In particular embodiments, the porous membrane 228 may include polytetrafluoroethylene (PTFE), although it is contemplated that other materials may be used in addition to PTFE or instead of PTFE. The porous membrane 228 may be treated with one or more coatings to provide designated properties. For example, the porous membrane 228 may be impregnated or wetted with a hydrophobic coating that impedes the flow of a polar liquid through the porous membrane 228 or with a hydrophilic coating that facilitates the flow of a polar liquid through the porous membrane 228. In some embodiments, the entire filter surface 230 or portions thereof are coated to have desired properties. For example, the filter surface 230 may be wetted with a hydrophobic coating to impedes the flow of a polar liquid into the porous membrane 228 or with a hydrophilic coating that facilitates the flow of a polar liquid into the porous membrane 228.

The porous membrane 228 may have a designated porosity. The porosity may represent the void or space within the porous membrane 228. By way of example, the porosity may be between a minimum porosity of 20% and a maximum porosity of 85%. The minimum porosity may be 25%, 30%, or 35%. In more particular embodiments, the minimum porosity may be 40%, 41%, 42%, 43%, 44%, 45%, 46%, 47%, 48%, 49%, or 50% or more. The maximum porosity may be 80%, 75%, or 70%. In more particular embodiments, the maximum porosity may be 69%, 68%, 67%, 66%, 65%, 64%, 63%, 62%, 61%, or 60% or less. One or more embodiments may have a porosity range that is between any of the minimum and maximum values noted above. For example, in some embodiments, the porous membrane has a porosity that is between 40% and 70%. In some embodiments, the porous membrane has a porosity that is between 50% and 65%. The porous membrane may have a substantially constant porosity throughout or, alternatively, may have different regions with different porosities. For example, the porous membrane 228 may include multiple membrane layers in which each membrane layer has a different porosity.

The porous membrane 228 may have a designated mean or average pore size. By way of example, the mean pore size may be between a minimum mean value of 1 µm and a maximum mean value of 100 µm. In some embodiments, the minimum mean pore size is 2 µm, 4 µm, 6 µm, 8 µm, or 10 µm. In certain embodiments, the minimum mean pore size is 11 µm, 12 µm, 13 µm, 14 µm, 15 µm, 16 µm, 17 µm, 18 µm, 19 µm, 20 µm or more. In some embodiments, the maximum mean pore size is 90 µm, 85 µm, 80 µm, 75 µm, or 70 µm. In certain embodiments, the maximum mean pore size is 65 µm or 60 µm. In particular embodiments, the maximum mean pore size is 59 µm, 58 µm, 57 µm, 56 µm, 55 µm, 54 µm, 53 µm, 52 µm, 51 µm, or 50 µm. In particular embodiments, the maximum mean pore size is 49 µm, 48 µm, 47 µm, 46 µm, 45 µm, 44 µm, 43 µm, 42 µm, 41 µm, or 40 µm or less. One or more embodiments may have a mean pore size that is between any of the minimum and maximum values noted above. For example, in some embodiments, the porous membrane has a mean pore size that is between 10 µm and 50 µm. In some embodiments, the porous membrane has a mean pore size that is between 20 µm and 40 µm.

The porosity and mean pore size of the porous membrane may be determined based on information provided by the manufacturer or vendor (e.g., specification for porous membrane material). In some cases, the porosity and mean pore size of the porous membrane may be determined based on industry accepted techniques for the intended application of the porous membrane (e.g., separating immiscible liquids). Such techniques may be described in Souhaimi et al., Membrane Distillation: Principles and Applications, Chapter 8: Membrane Characterization, Elsevier (2011) or in Nakao, Determination of Pore Size and Pore Size Distribution. 3. Filtration Membranes: Review, J. Membr. Sci., 96 (1994) 131-165.

The filter surface 230 may have a non-planar contour that forms or defines the receiving cavity 204. The filter surface 230 may include one or more different slopes 251, 252 that define portions of the filter surface 230. The slopes 251, 252 may cause a change in depth 250 of the receiving cavity. The depth 250 may be measured with respect to the cavity edge 209 or the reference plane 246. The slopes 251, 252 may correspond to portions of the filter surface 230 that are angled with respect to the gravitational force axis 248 and/or the reference plane 246. The slopes 251, 252 may be linear or non-linear such that the depth 250 of the receiving cavity 204 changes at a linear rate or a non-linear rate, respectively. A point along the filter surface 230 that corresponds to a maximum value of the depth 250 (or the maximum depth) of the receiving cavity 204 may represent a bottom 256 of the receiving cavity 204.

The receiving cavity 204 may be oriented with respect to a cavity axis 260. In the illustrated embodiment, the cavity axis 260 extends through a geometric center of the access opening 210 and the bottom 256 of the receiving cavity 204. The filter surface 230 may surround the cavity axis 260 such that the filter surface 230 is rotationally symmetrical about the cavity axis 260. For instance, the receiving cavity 204 may be an inverted right-circular cone. In other embodiments, the receiving cavity 204 may be conical, but may not define a right-circular cone. For example, the receiving cavity 204 may be an oblique circular cone. Yet in other embodiments, the access opening 210 has a polygonal profile such that the receiving cavity 204 has a pyramidal shape.

The shape of the receiving cavity 204 may be configured such that the filter surface 230 contacts a liquid mixture at different depths when the liquid mixture is depositing within the receiving cavity 204. The porous membrane 228 may be shaped such that the porous membrane 228 surrounds the liquid mixture and is capable of receiving portions of the liquid mixture at different depths.

The access opening 210 has a maximum diameter 262. In some embodiments, the maximum diameter 262 may represent a greatest distance between two points of the cavity edge 209. In some embodiments, the maximum diameter 262 may be a line that extends through the cavity axis 260 between two points of the cavity edge 209. The receiving cavity 204 may be shaped such that the maximum depth 250 is less than the maximum diameter 262. For example, an aspect ratio of the maximum diameter 262 to the maximum depth 250 may be at least 1.5:1. In certain embodiments, the aspect ratio of the maximum diameter 262 to the maximum depth 250 may be at least 2:1. In particular embodiments, the aspect ratio of the maximum diameter 262 to the maximum depth 250 may be at least 2.5:1. In particular embodiments, the aspect ratio of the maximum diameter 262 to the maximum depth 250 may be at least 3:1. By way of example, the maximum diameter 262 may be at most 10 mm, at most 8 mm, at most 6 mm, at most 5 mm, or at most 4 mm. By way of example, the maximum depth 250 may be at most 4 millimeters (mm), at most 3 mm, at most 2 mm, or at most 1 mm. In some embodiments, the receiving cavity 204 may be shaped to permit a user to view a droplet that is formed by one liquid after another liquid flows into the porous membrane 228.

In the illustrated embodiment, the filter surface 230 has a single inflection point at the bottom 256 such that the depth 250 is continuously reducing as the filter surface 230 extends from the bottom 256 to the cavity edge 209. In other embodiments, the filter surface 230 may have more than one inflection point. In such embodiments, the depth 250 may not continuously reduce and, instead, may have areas with increasing depths. Thus, the receiving cavity 204 may have more than one bottom and or have spaces that are separated from each other.

As shown, the slope 251 changes the depth 250 at a linear rate, and the slope 252 changes the depth 250 at a non-linear rate (e.g., exponential rate). Thus, with respect to the illustrated embodiment, a majority of the filter surface 230 has a slope that changes the depth 250 at a linear rate. In some embodiments, the filter surface 230 proximate to the bottom 256 has a radius of curvature. The slopes 251, 252 may be configured along with other parameters to form a droplet of a liquid within the receiving cavity 204. For example, the slopes 251, 252 may be configured to bead a polar liquid located at the bottom 256 of the receiving cavity 204.

FIGS. 8 and 9 illustrate first and second stages, respectively, of a filtering operation. In the first stage, a liquid mixture 270 has been deposited within the receiving cavity 204. As shown in FIG. 8, the liquid mixture 270 initially includes an emulsion of a first liquid 272 and a second liquid 274. In some embodiments, the first liquid 272 may form micro-droplets within the second liquid 274. For example, although only a few droplets of the first liquid 272 are shown in FIG. 8, the first liquid 272 may form tens, hundreds, or thousands of micro-droplets within the second liquid 274. The micro-droplets may have a variety of volumes (e.g., difference in an order of magnitude) when initially deposited into the receiving cavity 204 or the micro-droplets may have a substantially common volume. For example, the liquid mixture 270 and the corresponding micro-droplets may be similar to those used in emulsion-type applications. In some embodiments, the micro-droplets will contain individual assay reactions such as reverse transcription they are subsequently pooled into a single pot for the next step through the phase separation and pooling.

For illustrative purposes, the liquid mixture 270 has not begun to filter in FIG. 8, but it should be understood that filtering may begin immediately when the liquid mixture 270 contacts the filter surface 230. The first liquid 272 may be a polar liquid, such as an aqueous solution including a biological sample, and the second liquid 274 may be a non-polar liquid, such as a filler liquid (e.g., oil) from a DF device. Alternatively, the first liquid 272 may be a non-polar liquid, and the second liquid 274 may be a polar liquid. The receiving cavity 204 has a volume that is defined between the filter surface 230 and the access opening 210 or the reference plane 246 (FIG. 7).

In some embodiments, the receiving cavity 204 may have a volume that is less than 1000 µl. In some embodiments, the receiving cavity 204 may have a volume that is less than 750 µl or less than 500 µl. In certain embodiments, the receiving cavity 204 may have a volume that is less than 400 µl, less than 300 µl, less than 200 µl, or less than 150 µl. In particular embodiments, the receiving cavity 204 may have a volume that is less than 100 less than 90 µl, less than 80 µl, or less than 70 µl. Typically, the liquid mixture 270 has a volume that is less than the volume of the receiving cavity 204. For instance, the liquid mixture 270 may have a volume that is less than 200 µl, less than 150 µl, less than 100 µl, less than 90 µl, less than 80 µl, less than 70 µl, less than 60 µl, or less than 50 µl. In particular embodiments, the liquid mixture 270 may have a volume that is less than 40 µl, less than 30 µl, less than 20 µl, less than 15 µl, less than 14 µl, less than 13 µl, less than 12 µl, less than 11 µl, or less than 10 µl.

As shown, a volume of the second liquid 274 may be greater than a volume of the first liquid 272 within the liquid mixture 270. In other embodiments, the volume of the second liquid 274 may be less than the volume of the first liquid 272. By way of example, a volume ratio of the second liquid 274 to the first liquid 272 may be at least 1:1, at least 1.5:1, at least 2:1, at least 3:1, at least 4:1, at least 5:1, or more. In certain embodiments, the volume ratio of the second liquid 274 to the first liquid 272 may be at least 6:1, at least 8:1, at least 10:1, at least 12:1, at least 14:1, at least 16:1, at least 18:1, at least 20:1. In more particular embodiments, the volume ratio of the second liquid 274 to the first liquid 272 may be at least at least 22:1, at least 24:1, at least 26:1, at least 28:1, at least 30:1, at least 32:1, or more.

In some embodiments, the volume of the first liquid 272 is between 1 nanoliter (nl) and 10,000 nl. In some embodiments, the volume of the first liquid 272 is between 10 nanoliters (nl) and 5000 nl. In certain embodiments, the volume of the first liquid 272 is between 50 nanoliters (nl) and 1000 nl. In particular embodiments, the volume of the first liquid 272 is between 200 nanoliters (nl) and 500 nl. In some embodiments, the volume of the second liquid 274 is between 1 µl and 500 µl. In some embodiments, the volume of the second liquid 274 is between 2 µl and 200 µl. In certain embodiments, the volume of the second liquid 274 is between 4 µl and 100 µl. In particular embodiments, the volume of the second liquid 274 is between 5 µl and 50 µl, between 5 µl and 25 µl, or between 5 µl and 15 µl. By way of one example, the second liquid 274 may have a volume of about 10 µl, and the first liquid 272 may have a volume of about 300 nl. In such embodiments, the ratio of the volume of the second liquid 274 to the volume of the first liquid 272 is greater than or about equal to 30:1.

As shown in FIG. 8, the second liquid 274 separates the first liquid 272 into multiple sub-droplets 276. In some embodiments, the liquid mixture 270 may be characterized as an emulsion having multiple sub-droplets 276 (or micro-droplets). In other embodiments, the liquid mixture 270 may be substantially separated into two or more layers without sub-droplets being formed. As shown in FIG. 8, a contoured interface or boundary 282 may initially exist between the filter surface 230 and the liquid mixture 270.

FIG. 9 illustrates a latter second stage in which the second liquid 274 from the prior stage (FIG. 8) has flowed into the porous membrane 228. A dashed line 278 indicates a saturation boundary of the second liquid 274 within the porous membrane 228. As described herein, the filter surface 230 is configured to permit the second liquid 274 to flow from the receiving cavity 204 and into the porous membrane 228. For example, the pore size and/or porosity along the filter surface 230 may permit the second liquid 274 to flow through the filter surface 230 and into the absorption region 240 of the porous membrane 228. The filter surface 230 may have a surface property that permits the second liquid 274 to flow through there while impeding flow of the first liquid 272. As an example, the first liquid 272 may be a polar liquid that is repelled by a hydrophobic property of the filter surface 230. The hydrophobic property, however, does not impede the second liquid 274, which is permitted to flow into the porous membrane 228. As the second liquid 274 flows into the porous membrane 228, the sub-droplets 276 (FIG. 8) of the first liquid 272 may combine to form a droplet 285.

In some embodiments, the contoured filter surface 230 increases an amount of surface contact between the filter surface 230 and the liquid mixture 270. In some embodiments, the first and second liquids 272, 274 may have different densities such that the first and second liquids 272, 274 separate into different layers within the receiving cavity 204. In such embodiments, the shape of the filter surface 230 increases the likelihood that the filter surface 230 will contact the liquid having less density. For example, if the second liquid 274 has less density than the first liquid 272, the second liquid 274 may form a layer on top of the first liquid 272. Nonetheless, the filter surface 230 is able to contact the second liquid 274 due to the non-planar contour such that the porous membrane 228 is capable of absorbing the second liquid 274.

Embodiments set forth herein may be configured to achieve an acceptable separation or filtering of the immiscible liquids within a liquid mixture. In some embodiments, one of the liquids may be effectively isolated from the other liquids. For example, embodiments may be able to separate or filter the second liquid 274 such that at least 75% of the second liquid 274 is removed from the receiving cavity 204. The second liquid 274 may be absorbed by the porous membrane 228 and/or permitted to exit the porous membrane 228 into another space through the outer surface 238. Certain embodiments may remove at least 85% of the second liquid 274 from the receiving cavity 204. Particular embodiments may remove at least 95% or at least 97% of the second liquid 274 from the receiving cavity 204. More particular embodiments may remove at least 98% or at least 99% of the second liquid 274 from the receiving cavity 204.

The porous membrane 228 may absorb the second liquid 274 at a designated absorption rate. The absorption rate of a particular liquid may be based environmental conditions (e.g., temperature and pressure of surrounding environment), properties of the liquids within the liquid mixture, properties of the filter surface and porous membrane, and a shape of the filter surface 230. For example, the absorption rate may increase with an increase in the slope 251 of the filter surface 230.

By way of example, embodiments may be capable of removing at least 75% of the second liquid 274 within 30 seconds, at least 85% of the second liquid within 30 seconds, at least 95% of the second liquid within 30 seconds, at least 98% of the second liquid within 30 seconds, or at least 99% of the second liquid within 30 seconds. More particularly, embodiments may be capable of removing at least 85% of the second liquid 274 within 20 seconds, at least 85% of the second liquid within 10 seconds, or at least 85% of the second liquid within 5 seconds. Yet more particularly, embodiments may be capable of removing at least 95% of the second liquid 274 within 20 seconds, at least 95% of the second liquid within 10 seconds, or at least 95% of the second liquid within 5 seconds. Compared to conventional separating processes that use centrifuges, at least some embodiments may substantially reduce the time, complexity, and cost required for separating the immiscible liquids.

After the designated amount of time (e.g., seconds, minutes, hours), a liquid remaining within the receiving cavity 204 (referred to as the remaining liquid or the remainder 286) may be removed. The remaining liquid 286 includes the droplet 285 of the first liquid 272 and, possibly, a minor amount or residue of the second liquid 274 such that the first liquid 272 is effectively isolated from the second liquid 274. For instance, the second liquid 274 may comprise at most 25% of the volume of the remaining liquid 286 or at most 15% of the volume of the remaining liquid 286. More particularly, the second liquid 274 may comprise at most 10% of the volume of the remaining liquid 286, at most 5% of the volume of the remaining liquid 286, or at most 1% of the volume of the remaining liquid 286.

In some embodiments, the shape of the filter surface 230 and the surface properties may cause the droplet 285 to bead up within the receiving cavity 204. For example, an exterior surface of the droplet 285 has a convex shape in FIG. 9. In such embodiments, a user may be able to visually locate the droplet 285 and insert an instrument into the receiving cavity 204 and into the droplet 285. In some cases, the instrument may be capable of withdrawing only the liquid from the droplet 285 and thereby leaving the second liquid 274 within the receiving cavity 204.

In other embodiments, a second liquid mixture (not shown) may be added to the receiving cavity 204 after the second liquid 274 is filtered, but prior to removing the remaining liquid 286. Similar to the liquid mixture 270, the second liquid mixture may include a first liquid (e.g., polar liquid) and a second liquid (e.g., non-polar liquid). The first liquid may or may not have a different composition (e.g., different biological sample) than the first liquid 272. Again, the phase-separation device 200 may allow the second liquid to flow into the porous membrane 228 and impede flow of the first liquid into the porous membrane 228. In such embodiments, two different first liquids (e.g., two different biological samples) may be combined within the receiving cavity 204.

In alternative embodiments, the filter surface 230 does not have a curved contour. For example, the filter surface 230 may be flat or planar such that the receiving cavity is disc-shaped, cubic, etc. Optionally, the phase-separation device 200 may include walls (not shown) that are coupled to the filter surface 230 that define outer boundaries of the receiving cavity 204. Nonetheless, in such embodiments, the filter surface 230 may permit the second liquid 274 to flow into the porous membrane 228 and impede flow of the first liquid 272 into the porous membrane 228. In some embodiments, the droplet 285 of the first liquid 272 may bead up along the filter surface 230.

Figure 13:
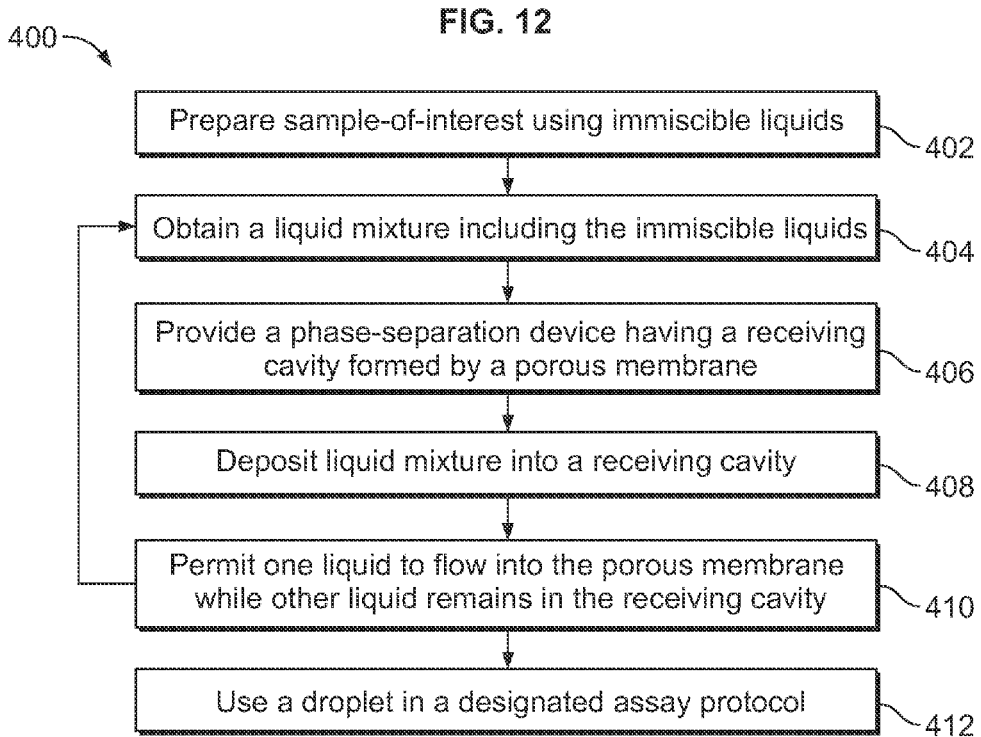
FIG. 13 is a flowchart illustrating a method in accordance with an embodiment.

FIG. 10 is a perspective view of a filter body 300 that may constitute a phase-separation device alone or be part of a phase-separation device, such as the phase-separation device 350 (FIG. 13). FIG. 11 is a cross-section of the filter body 300 taken along the line 11-11 in FIG. 10. The filter body 300 may be similar to the filter body 226 (FIG. 6). For example, the filter body 300 includes a porous membrane 302 having a filter surface 304 that defines a corresponding receiving cavity 306 of the filter body 300. Like the receiving cavity 204 (FIG. 6), the receiving cavity 306 may be an inverted right-circular cone. However, the receiving cavity 306 may have other shapes in other embodiments. In an exemplary embodiment, the filter body 300 is formed exclusively from the porous membrane 302. In other embodiments, however, the filter body 300 may include separate components that are assembled together. For example, the filter body 300 may include a cap or rim that is mounted onto the porous membrane 302.

The filter body 300 has an exterior surface 308 that defines a shape of the filter body 300. The exterior surface 308 may be shaped such that the filter body 300 may, for instance, fit within a cavity of a plate or tube (not shown). The filter body 300 has an outer diameter 326. As shown in FIG. 11, the filter body 300 includes a top body portion 322 and a bottom body portion 324. In the illustrated embodiment, the outer diameter 326 is uniform or constant along the top body portion 322. However, the outer diameter 326 decreases or tapers as the bottom body portion 324 extends away from the top body portion 322.

The filter body 300 includes an access opening 310. In the illustrated embodiment, the access opening 310 has a circular profile. In other embodiments, however, the access opening 310 may have different profiles. For instance, the access opening 310 may be polygonal, semi-circular, etc. As shown in FIG. 11, the access opening 310 has a maximum diameter 312, and the receiving cavity 306 has a depth 314. In the illustrated embodiment, the receiving cavity 306 is shaped such that a maximum depth 314 is more than the maximum diameter 312. For example, an aspect ratio of the maximum depth 314 to the maximum diameter 312 may be at least 1.5:1. In certain embodiments, the aspect ratio of the maximum depth 314 to the maximum diameter 312 may be at least 2:1. In particular embodiments, the aspect ratio of the maximum depth 314 to the maximum diameter 312 may be at least 2.5:1. In particular embodiments, the aspect ratio of the maximum depth 314 to the maximum diameter 312 may be at least 3:1 or at least 5:1. Accordingly, compared to the filter surface 230 (FIG. 6), the filter surface 304 has a steeper slope. In some embodiments, the filter surface 304 may provide a larger contact area between a liquid mixture and the filter surface 304.

As described above with respect to the phase-separation device 200 (FIG. 5), the filter body 300 is configured to receive a liquid mixture (not shown) within the receiving cavity 306. The porous membrane 302 may absorb one of the liquids within the liquid mixture and impede flow of another liquid such that a droplet of the other liquid is formed within the receiving cavity 306. Characteristics and properties of the porous membrane 302 and the filter surface 304 may be similar or identical to the porous membrane 228 and the filter surface 230, respectively. The filter body 300 may have similar absorption rates as the porous membrane 228. In some embodiments, the absorption rate may be greater than the absorption rate of the porous membrane 228.

Figure 12:
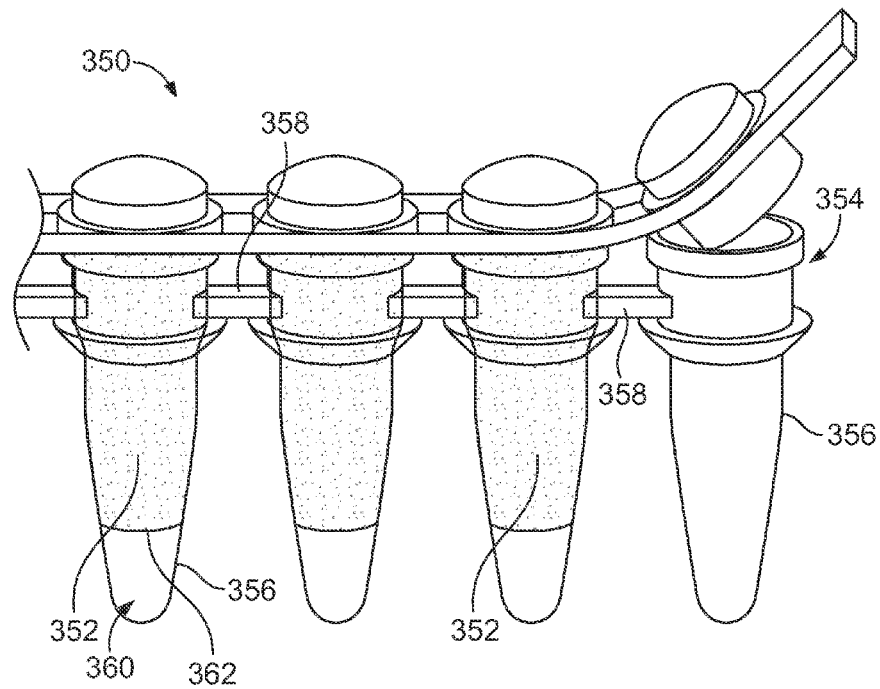
FIG. 12 is an illustration of a phase-separation device in accordance with an embodiment that includes a plurality of filter bodies.

FIG. 12 is an illustration of a phase-separation device 350 in accordance with an embodiment that includes a plurality of filter bodies 352. The filter bodies 352 may be similar or identical to the filter bodies 300 (FIG. 10). As shown, the phase-separation device 350 also includes a discrete support frame 354. The support frame 354 includes a plurality of tubes or vials 356 and a plurality of links 358 that join the tubes 356 to one another. The links 358 may have some flexibility such that the tubes 356 may be movable with respect to one another. Each of the tubes 356 has an interior surface that is sized and shaped to receive one of the filter bodies 352. As shown, a reservoir 360 is formed between a bottom 362 of the filter body 352 and the interior surface of the tube 356. In some embodiments, the reservoir 360 may be configured to receive a liquid that flows through the filter bodies 352.

In other embodiments, the phase-separation device 350 may include a single filter body 352 and a single tube 356. In such embodiments, the phase-separation device 350 may be loaded into a centrifuge to facilitate the separation or filtering of the liquid mixture. However, centrifuges are not necessarily limited to embodiments that only include a single filter body. It is contemplated that centrifuges may be used with other embodiments, such as the phase-separation device 200 (FIG. 5). Yet still in other embodiments, a vacuum source (not shown) may be provided to induce flow of a liquid into the porous membrane. The vacuum source may provide air to push the liquid therethrough or, alternatively, may draw the liquid through the porous membrane.

FIG. 13 is a flowchart illustrating a method 400 in accordance with an embodiment. Although FIG. 13 provides one example of a method that may carried in accordance with one or more embodiments, it should be understood that embodiments are not limited to the steps illustrated in FIG. 13. Steps may be omitted, steps may be modified, and/or other steps may be added. Moreover, steps described herein may be combined, steps may be performed simultaneously, steps may be performed concurrently, steps may be split into multiple sub-steps, steps may be performed in a different order, or steps (or a series of steps) may be re-performed in an iterative fashion. One or more steps may be performed manually. One or more steps may be performed automatically using an automated system.

The method 400 includes preparing, at 402, a sample-of-interest using a plurality of immiscible liquids. For example, the sample-of-interest may be a biological sample (e.g., nucleic acids) suspended within a first liquid. As described above, the first liquid may be a polar liquid (e.g., aqueous solution). For some protocols, the first liquid may be confined within a DF device in the form of droplets that are surrounded by a second liquid (e.g., non-polar liquid). The droplets of the first liquid may be transported through the second liquid by electrowetting-mediated operations in order to prepare or modify the biological sample. In particular embodiments, the biological sample includes fragments of nucleic acids that are configured to be used during a SBS protocol.

The method 400 also includes obtaining, at 404, a liquid mixture that includes the first liquid and the second liquid. The obtaining operation 404 may include removing a designated volume of the first and second liquids from, for example, the DF device. By way of example, the obtaining operation 404 may include inserting a nozzle of a pipettor into a cavity of the DF device and withdrawing a designated volume of the liquid mixture. In some embodiments, a majority of the designated volume includes the second liquid and a minority of the designated volume includes the first liquid. In particular embodiments, the first liquid may represent only a fraction of the total volume, such as less than 25% of the total volume.

Optionally, the obtaining, at 404, may also include drawing a third liquid into the liquid mixture. For example, after the first and second liquids are drawn into a pipettor, the pipettor may be transported to another liquid source that includes a third liquid. The third liquid may include a polar liquid that is miscible with respect to the first liquid. More specifically, the third liquid may be an aqueous solution (e.g. buffer solution) that is capable of mixing homogeneously with the first liquid. In some embodiments, the third liquid may be configured to react with and/or modify the sample within the first liquid. In particular embodiments, the third liquid may be configured to dilute or stabilize one or more contents from the first liquid. Thus, the third liquid need not react with or chemically modify the contents of the first liquid. Collectively, the first, second, and third liquids may form an emulsion. For simplicity, the first and third liquids may be referred to as the first liquid or as the combined liquid.

At 406, a phase-separation device may be provided. The phase-separation device may be similar or identical to the phase-separation devices described herein. For example, the phase-separation device may include a porous membrane having a filter surface. The filter surface may have a non-planar contour that forms a receiving cavity. The method 400 may also include depositing, at 408, the liquid mixture into the receiving cavity of the porous membrane. The deposition, at 408, may include depositing a measured volume of the liquid mixture. The measured volume may be an approximate value that is determined by, for example, an instrument used to transfer the liquid mixture to the phase-separation device. For instance, pipettors may be configured to draw an approximate or measured volume (e.g., about 10 µl) from the DF device. Optionally, pipettors may be configured to drawn an additional volume (e.g., another 10 µl)

of the third liquid. The measured volume within the instrument may be equal to or less than a volume of the receiving cavity.

The filter surface along the receiving cavity may be configured to impede flow of the first liquid (or combined liquid) through the filter surface. For example, if the first liquid is a polar liquid, the filter surface and/or the porous membrane may have a hydrophobic property that impedes flow of the polar liquid into the porous membrane. However, the filter surface may permit flow of the second liquid into the porous membrane. Accordingly, the method 400 may include permitting, at 410, the second liquid to flow into the porous membrane. A remainder of the liquid mixture may form a droplet within the receiving cavity.

In some embodiments, permitting, at 410, the second liquid to flow into the porous membrane is performed without moving the phase-separation device. For example, the phase-separation device may be placed on a surface or within a multi-well plate or tube. The second liquid may flow into the porous membrane without moving or agitating the phase-separation device or without generating a centripetal force. In other words, the phase-separation device may be still as the second liquid flows into the porous membrane.

However, in other embodiments, permitting, at 410, the second liquid to flow into the porous membrane may include facilitating or urging the flow of the second liquid. For example, the phase-separation device may be positioned within a centrifuge. The centrifuge may generate a centripetal force that causes the liquid mixture to press against the filter surface. The centripetal force may urge the second liquid into the porous membrane. Alternatively, the phase-separation device may be coupled to an agitation sub-system that moves the phase-separation device. For example, the agitation sub-system may shake or vibrate the phase-separation device to shake or vibrate the liquid mixture within the receiving cavity. In some cases, the shaking/vibrating may facilitate separating the liquid mixture.

The method 400 may include removing the droplet, at 412, from the receiving cavity. For example, a nozzle of an instrument may be manually or automatically inserted into the receiving cavity and fluidically couple to the droplet. The droplet may be drawn into the instrument. The instrument may be carried, such as by a user or a robotic arm, to a designated location. The instrument, such as a pipettor, may then deposit the droplet into another system that utilizes the droplet. For example, the instrument may deposit the droplet within an SBS system. Alternative embodiments may not use a separate instrument. For example, in other embodiments, an end of a tube may have a fixed position within the receiving cavity. After the liquid mixture has been deposited into the receiving cavity and a designated period of time has elapsed, a flow of the droplet into through the tube may be induced (e.g., using a vacuum source). The droplet may be directed to a designated location within the assay system. At 414, the droplet may be used during a designated assay protocol, such as SBS.

Figure 14:
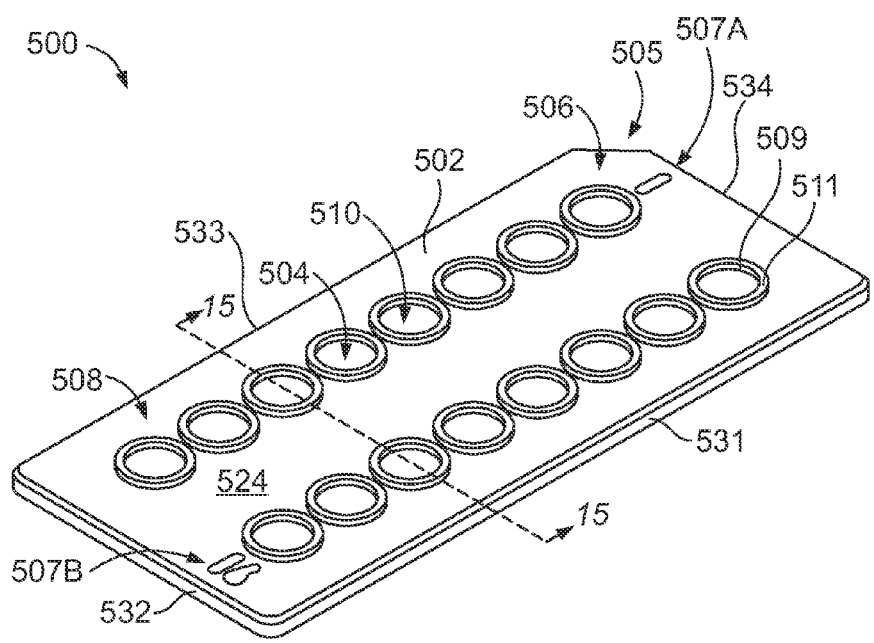
FIG. 14 is a perspective view of a phase-separation device in accordance with an embodiment.
Figure 15:
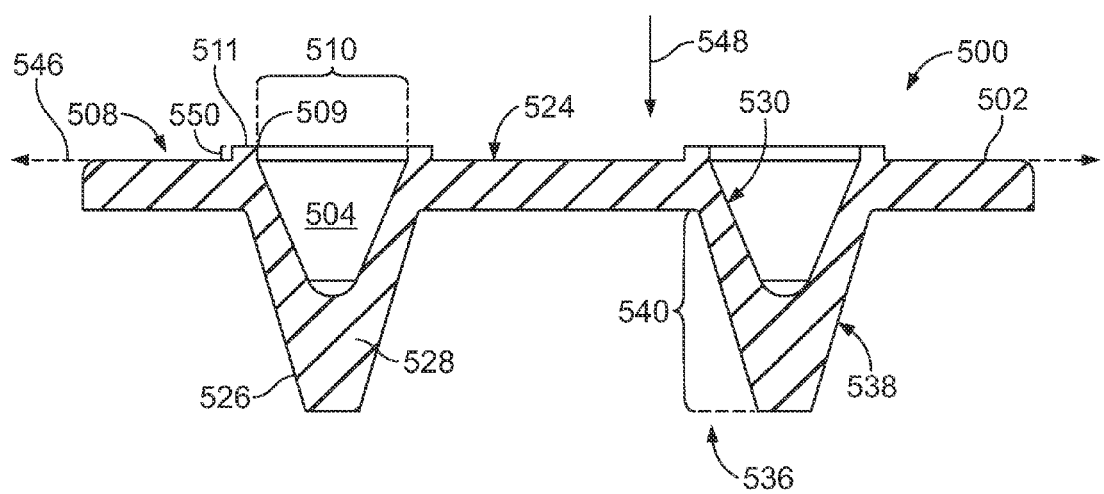
FIG. 15 is a cross-section of the phase-separation device of FIG. 14.
Figure 18:
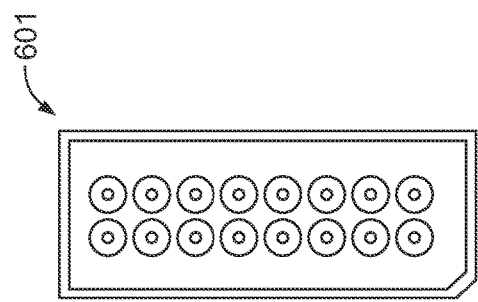
FIG. 18 is a bottom plan view of the phase-separation device of FIG. 16.
Figure 17:
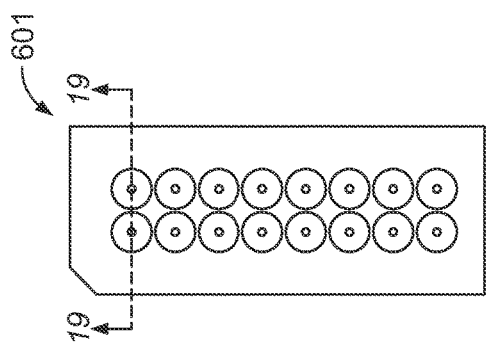
FIG. 17 is a top plan view of the phase-separation device of FIG. 16.
Figure 16:
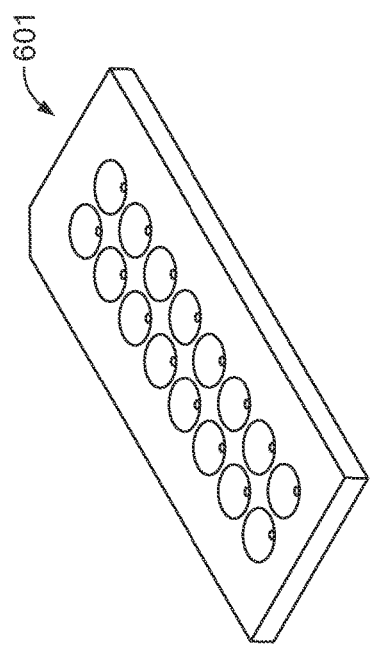
FIG. 16 is a perspective view of a phase-separation device in accordance with an embodiment.
Figure 19:
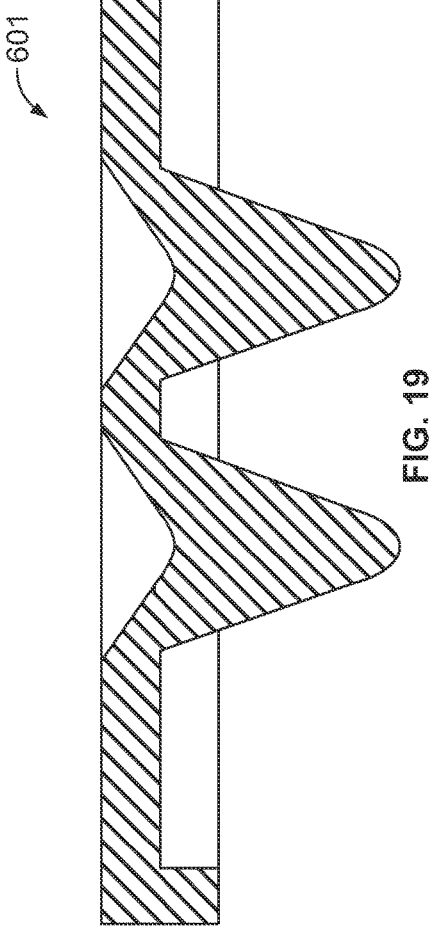
FIG. 19 illustrates a cross-section of the phase-separation device of FIG. 16 taken along the line A-A of FIG. 17.

FIG. 14 is a perspective view of a phase-separation device 500 in accordance with an embodiment, and FIG. 15 is a cross-section of the phase-separation device 500 taken along the line 15-15. The phase-separation device 500 may be similar to the phase-separation device 125 (FIG. 1) or the phase-separation device 200 (FIG. 5). With respect to FIG. 14, the phase-separation device 500 includes a support frame 502 and multiple receiving cavities 504 that are coupled to the support frame 502. Each of the receiving cavities 504 is sized and shaped to receive a designated amount of a liquid mixture. The support frame 502 extends between and joins the receiving cavities 504. The support frame 502 may hold the receiving cavities 504 in fixed positions with respect to one another.

The receiving cavities 504 may be positioned in a designated or predetermined array 506. As shown, the array 506 is a two-dimensional array, but the array 506 may be one dimensional in other embodiments. Similar to the phase-separation device 200 (FIG. 5), the number and positions of the receiving cavities 504 in the array 506 may be based on a designated protocol that utilizes the phase-separation device 500.

The phase-separation device 500 includes an operating or active side 508 that is configured to face or be accessible to a user of the phase-separation device 500. The receiving cavities 504 have respective cavity edges 509 that define access openings 510 of the receiving cavities 504. The receiving cavities 504 open to the operating side 508. In the illustrated embodiment, the support frame 502 is a substantially two-dimensional structure. For example, the support frame 502 may be panel-shaped or board-shaped. The operating side 508 has a side surface 524 that is substantially planar, except for device walls or projections 511 that define the cavity edges 509. In other embodiments, the side surface 524 may not be planar. For example, the support frame 502 may include a plurality of bridges or links that extend between and join the receiving cavities 504. The phase-separation device 500 may have body edges 531-534 that define a profile of the phase-separation device 500. As shown, the profile is substantially rectangular.

Embodiments may have one or more orientation features. As used herein, an "orientation feature" includes a visually identifiable feature that may be used to determine an orientation of the phase-separation device. In particular embodiments, the orientation feature is a structural feature. For example, the phase-separation device 500 includes a keying feature 505, which visually indicates to a user the orientation of the phase-separation device 500. Alternatively, the phase-separation device 500 may be positioned within a seating space or holder. In such embodiments, the keying feature 505 may ensure that the phase-separation device 500 has the proper orientation within the seating space. In some embodiments, the phase-separation device 500 may also include a numerical identifier 507. Similar to the keying feature 505, the numerical identifiers 507 may visually indicate to a user the orientation of the phase-separation device 500. In the illustrated embodiment, the numerical identifier 507A identifies a first receiving cavity 504, and the numerical identifier 507B identifies a last (or $16^{th}$) receiving cavity 504.

FIG. 15 is a cross-section of the phase-separation device 500 taken along the line 15-15 in FIG. 14. In some embodiments, the operating side 508 or the side surface 524 may coincide with a reference plane 546. In the illustrated embodiment, the device walls 511 that define the cavity edges 509 and corresponding access openings 510 may project an elevation or height 550 above the reference plane 546.

In an exemplary embodiment, when the phase-separation device 500 is operably positioned for receiving a liquid mixture within the receiving cavities 504, a gravitational force axis 548 may extend normal to the reference plane 546. However, it should be understood that the phase-separation device 500 is not required to have a particular orientation with respect to gravity and may have other orientations in other embodiments. For example, the phase-separation device 500 may be tilted (e.g., 30°, 45°, etc.) with respect to the reference plane 546 shown in FIG. 15 when filtering liquids in some embodiments. It is also contemplated that the phase-separation device 500 could be rotated more extensively (e.g., 90°, 180°, etc.) in effectively closed systems.

Similar to the phase-separation device 200 (FIG. 5), the phase-separation device 500 may also include filter bodies 526. Each of the filter bodies 526 may include a porous membrane 528 having a filter surface 530 that defines a corresponding receiving cavity 504. The porous membrane 528 may be similar or identical to the porous membrane 228 and may have similar or identical membrane characteristics (e.g., pore size, porosity, etc.) as described above. The filter bodies 526 may have fixed positions with respect to each other. In an exemplary embodiment, the phase-separation device 500 includes a unitary body of the porous membrane 528. The unitary body of the porous membrane 528 may be shaped to form each of the filter bodies 526 and the support frame 502 of the phase-separation device 500. In other embodiments, however, the phase-separation device 500 may include separate components that are assembled together. For example, the support frame may include links (e.g., plastic or metal) that extend between and join separate filter bodies 526 that each comprise the porous membrane 528.

The phase-separation device 500 includes a mounting side 536 that is generally opposite the operating side 508. The filter bodies 526 are positioned along the mounting side 536. Each of the filter bodies 526 has an outer surface 538. The filter bodies 526 may form corresponding absorption regions 540 that are generally defined between the outer surface 538 and the filter surface 530 of the respective filter body 526. The absorption region 540 is located adjacent to the receiving cavity 504 and may represent a space of the porous membrane 528 that absorbs a liquid from the receiving cavity 504. The absorption region 540 may be located generally below the corresponding receiving cavity 504 or access opening 510. A thickness of a respective filter body 526 (or absorption region 540) is defined between the outer surface 538 and the filter surface 530. The thickness is not uniform in the illustrated embodiment. In some embodiments, the thickness and/or a volume of the absorption region 540 is greater than a volume of the receiving cavity 504. In other embodiments, however, the thickness and/or volume of the absorption region 540 is less than or equal to a volume of the receiving cavity 504.

In certain embodiments, the filter bodies 526 have designated shapes and are positioned relative to one another to permit the filter bodies 526 to be inserted into corresponding wells of a multi-well plate (not shown). In such embodiments, the multi-well plate may support the phase-separation device 500 and hold the phase-separation device 500 in a substantially stationary position. The wells (not shown) of the multi-well plate may also provide a space for receiving any liquid that flows entirely through the filter bodies 526 as described below.

Figure 20:
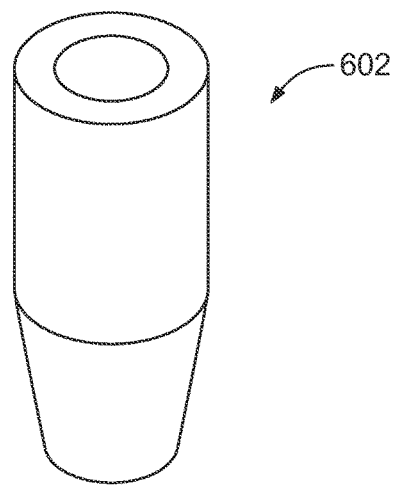
FIG. 20 is a perspective view of a phase-separation device in accordance with an embodiment.
Figure 21:
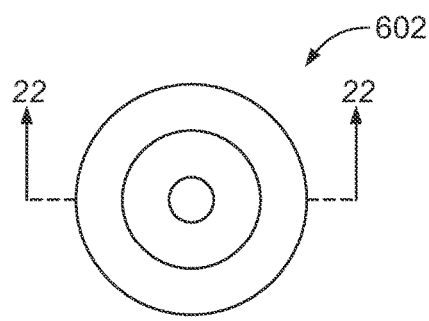
FIG. 21 is a top plan view of the phase-separation device of FIG. 20.
Figure 22:
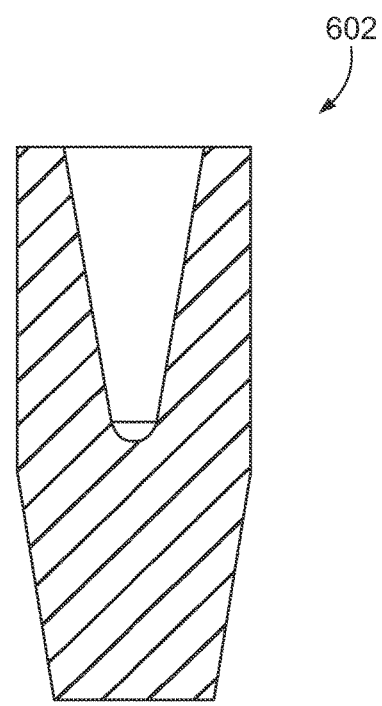
FIG. 22 illustrates a cross-section of the phase-separation device of FIG. 20 taken along the line A-A of FIG. 21.
Figure 23:
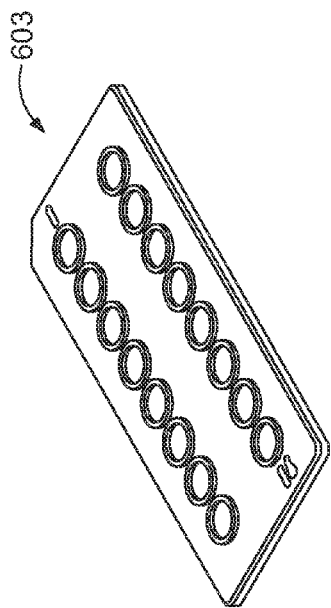
FIG. 23 is a perspective view of a phase-separation device in accordance with an embodiment.
Figure 24:
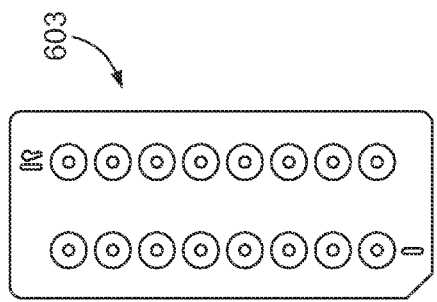
FIG. 24 is a bottom plan view of the phase-separation device of FIG. 23.
Figure 25:
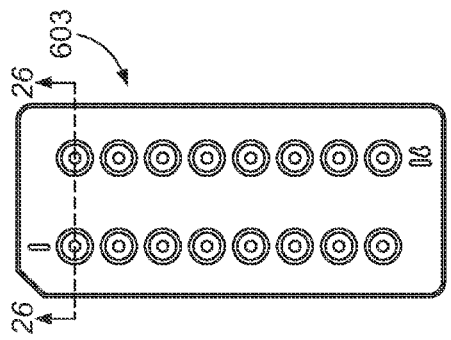
FIG. 25 is a top plan view of the phase-separation device of FIG. 23.
Figure 26:
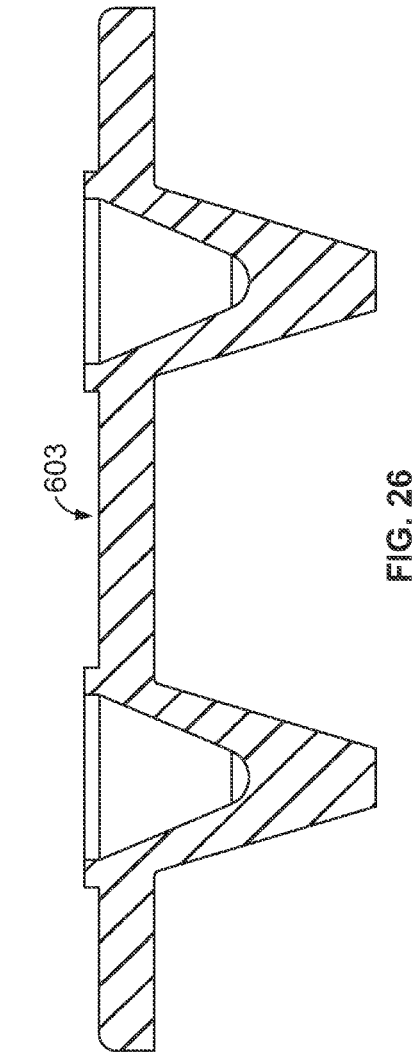
FIG. 26 illustrates a cross-section of the phase-separation device of FIG. 16 taken along the line A-A of FIG. 25.

FIGS. 16-19 illustrate a phase-separation device 601 in accordance with one embodiment. FIGS. 20-22 illustrate a phase-separation device 602 in accordance with one embodiment, FIGS. 23-26 illustrate a phase-separation device 603 in accordance with one embodiment. The phase-separation devices 601-603 may have similar characteristics and features as other embodiments described herein. For example, each of the phase-separation devices 601-603 may comprise PTFE (e.g., PTFE 10532). In particular embodiments, the phase-separation devices 601-603 may be unitary bodies of PTFE such that the entire phase-separation device 601-603, except for an optional impregnated liquid and/or an external coating or finish, may comprise PTFE. As shown, FIGS. 17, 19, 22, 25, and 26 indicate different dimensions of the corresponding devices. Unless otherwise specified, the dimensions are in millimeters. These dimensions and tolerances (and other dimensions and tolerances described with respect to other embodiments) may be interpreted per American Society of Mechanical Engineers (ASME) Y14.5M-1994. The dimensions may exist before or after a finishing process.

Figure 27:
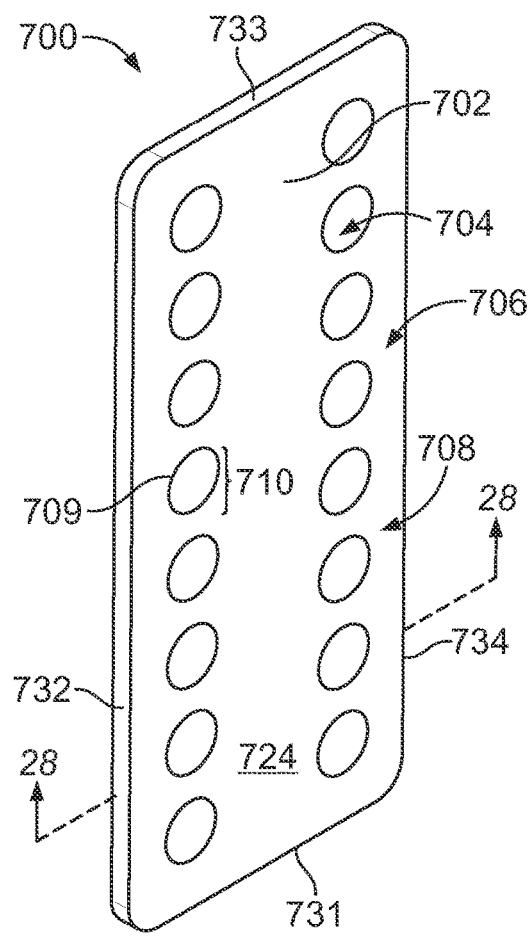
FIG. 27 is a perspective view of a phase-separation device in accordance with an embodiment.

FIG. 27 is a perspective view of a phase-separation device 700 in accordance with an embodiment. The phase-separation device 500 may be similar to the phase-separation device 125 (FIG. 1), the phase-separation device 200 (FIG. 5), or the phase-separation device 500 (FIG. 14). With respect to FIG. 27, the phase-separation device 700 includes a support frame 702 and multiple receiving cavities 704 that are coupled to the support frame 702. Each of the receiving cavities 704 is sized and shaped to receive a designated amount of a liquid mixture. The support frame 702 extends between and joins the receiving cavities 704. The support frame 702 may hold the receiving cavities 704 in fixed positions with respect to one another.

The receiving cavities 704 may be positioned in a designated or predetermined array 706. The array 506 may be one-, two-, or three-dimensional array. Similar to the phase-separation devices 200, 500, the number and positions of the receiving cavities 704 in the array 706 may be based on a designated protocol that utilizes the phase-separation device 700. The phase-separation device 700 includes an operating or active side 708 that is configured to face or be accessible to a user of the phase-separation device 700. The receiving cavities 704 have respective cavity edges 709 that define access openings 710 of the receiving cavities 704. The receiving cavities 704 open to the operating side 708. In the illustrated embodiment, the support frame 702 is a substantially two-dimensional structure. For example, the support frame 702 may be panel-shaped or board-shaped. In other embodiments, the support frame 702 may be a three-dimensional structure. For example, the support frame 702 may be stair-shaped and one or more groups of the receiving cavities 704 may have different elevations.

The operating side 708 has a side surface 724 that is substantially planar, except for the receiving cavities 704. In other embodiments, the side surface 724 may not be planar. For example, the support frame 702 may include a plurality of bridges or links that extend between and join the receiving cavities 704. The phase-separation device 700 has body edges 731-734 that define a profile of the phase-separation device 700. As shown, the profile is substantially rectangular, but the profile may have other shapes in other embodiments.

Figure 28:
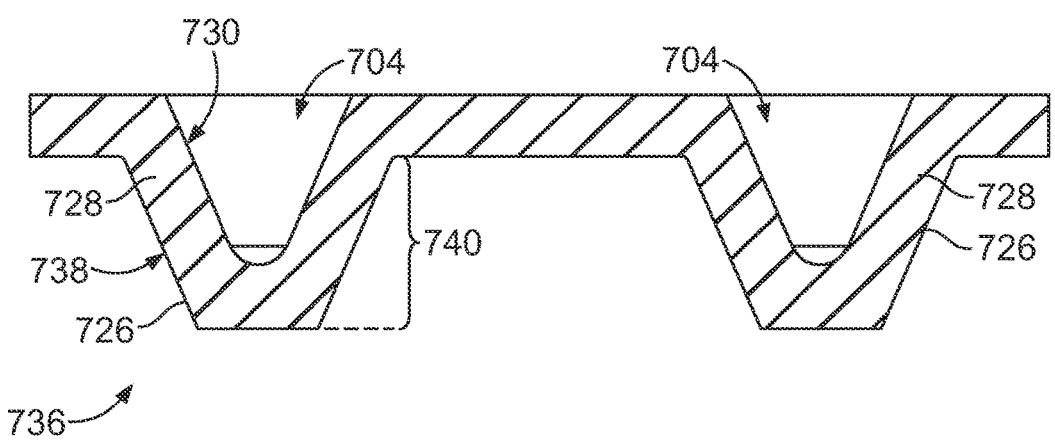
FIG. 28 is a cross-section of the phase-separation device of FIG. 27 taken along the line 28-28 in FIG. 27.

FIG. 28 is a cross-section of the phase-separation device 700 taken along the line 28-28 in FIG. 27. In some embodiments, the operating side 708 or the side surface 724 may coincide with a reference plane 746. Similar to the phase-separation devices 200, 500, the phase-separation device 700 may also include filter bodies 726. Each of the filter bodies 726 may include a porous membrane 728 having a filter surface 730 that defines a corresponding receiving cavity 704. The porous membrane 728 may be similar or identical to the porous membrane 228 or 528 and may have similar or identical membrane characteristics (e.g., pore size, porosity, etc.) as described above. The filter bodies 726 may have fixed positions with respect to each other. In an exemplary embodiment, the phase-separation device 700 includes a unitary body of the porous membrane 728. The unitary body of the porous membrane 728 may be shaped to form each of the filter bodies 726 and the support frame 702 of the phase-separation device 700. In other embodiments, however, the phase-separation device 700 may include separate components that are assembled together. For example, the support frame may include links (e.g., plastic or metal) that extend between and join separate filter bodies 726 that each comprise the porous membrane 728.

The phase-separation device 700 includes a mounting side 736 that is generally opposite the operating side 708. The filter bodies 726 are positioned along the mounting side 736. Each of the filter bodies 726 has an outer surface 738. The filter bodies 726 may form corresponding absorption regions 740 that are generally defined between the outer surface 738 and the filter surface 730 of the respective filter body 726. The absorption region 740 is located adjacent to the receiving cavity 704 and may represent a space of the porous membrane 728 that absorbs a liquid from the receiving cavity 704. The absorption region 740 may be located generally below the corresponding receiving cavity 704 or access opening 710. A thickness of a respective filter body 726 (or absorption region 740) is defined between the outer surface 738 and the filter surface 730 and may be configured to have a designated volume for the absorption region 740. In some embodiments, a volume of the absorption region 740 is less than a volume of the receiving cavity 704. In other embodiments, however, the volume of the absorption region 740 is greater than or equal to the volume of the receiving cavity 704.

In certain embodiments, the filter bodies 726 have designated shapes and are positioned relative to one another to permit the filter bodies 726 to be inserted into corresponding wells of a multi-well plate (not shown). In such embodiments, the multi-well plate may support the phase-separation device 700 and hold the phase-separation device 700 in a substantially stationary position. The wells (not shown) of the multi-well plate may also provide a space for receiving any liquid that flows entirely through the filter bodies 726 as described below.

Figure 29:
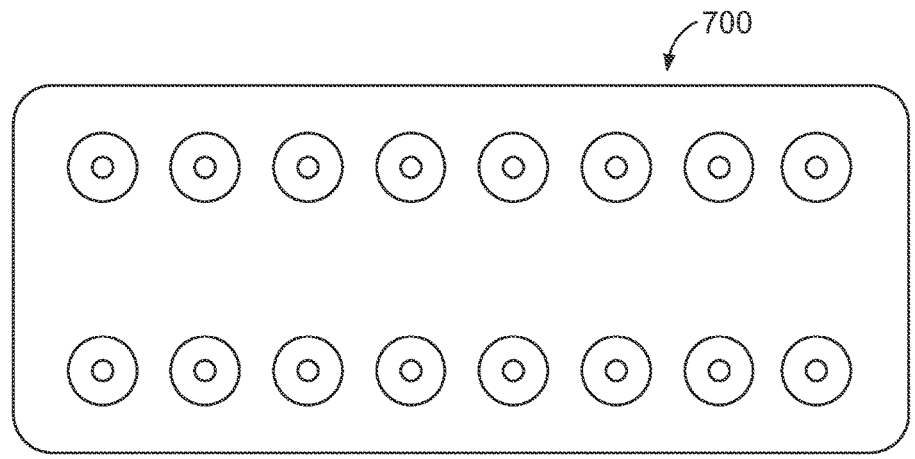
FIG. 29 is a plan view of the phase-separation device of FIG. 27.
Figure 30:
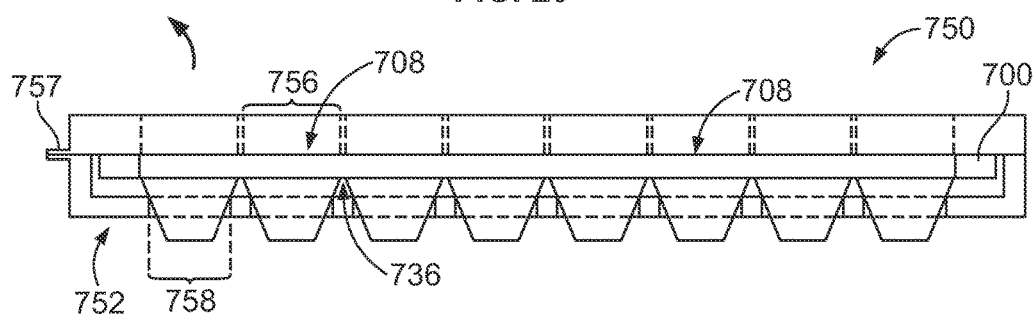
FIG. 30 is a side view of an assembly formed in accordance with an embodiment that includes the phase-separation device.

FIG. 29 is a plan view of the phase-separation device 700. FIG. 30 is a side view of an assembly 750 that includes the phase-separation device 700. The assembly 750 may also be referred to as a phase-separation assembly. The assembly 750 also includes a discrete support structure 752 that is configured to hold the phase-separation device 700. In the illustrated embodiment, the support structure 752 includes a cover 754 and a base 756 that are rotatably coupled to each other. The cover 754 is configured to extend along the operating side 708, and the base 756 is configured to extend along the mounting side 736 or at least a portion of the mounting side 736. The support structure 752 may be configured to increase a structural integrity (e.g., strength) of the phase-separation device 700 such that the phase-separation device 700 is less likely to break during transfer (e.g., shipping), storage, and/or use. In the illustrated embodiment, the cover and the base 756 are rotatably couple along a hinge 757. When the support structure 752 is in a closed position (as shown in FIG. 30), the cover and base 754, 756 may form an interference fit (e.g., snap-fit) such that the cover and base 754, 756 are not likely to be inadvertently separated.

In some embodiments, the support structure 752 is configured to hold the phase-separation device 750 during transfer or shipping, but allow the phase-separation device 750 to be removed prior to use. For example, the cover 754 and/or the base 756 may be separable. In other embodiments, however, the support structure 752 may also be used during use of the phase-separation device 750. For example, the cover 754 may include optional passages or openings 756 (indicated by dashed lines) that are positioned to align with the receiving cavities 704. Optionally, the base 756 may include openings 758 that allow the filter bodies 726 to extend therethrough. In such embodiments, the filter bodies 726 may be positioned within the wells of a multi-well plate, wherein the base 756 would be positioned between the multi-well plate and the phase-separation device 700. In other embodiments, the base 756 may receive and enclose the filter bodies 726 within a common cavity that is defined by the base 756. In such embodiments, it may be necessary to remove the base 756 prior to use of the phase-separation device 700. Alternatively, the phase-separation device 700 may be used while the filter bodies 726 are disposed within the common cavity. The cavity may receive the second liquid if the second liquid exits the outer surface of the filter bodies 726.

Figure 31:
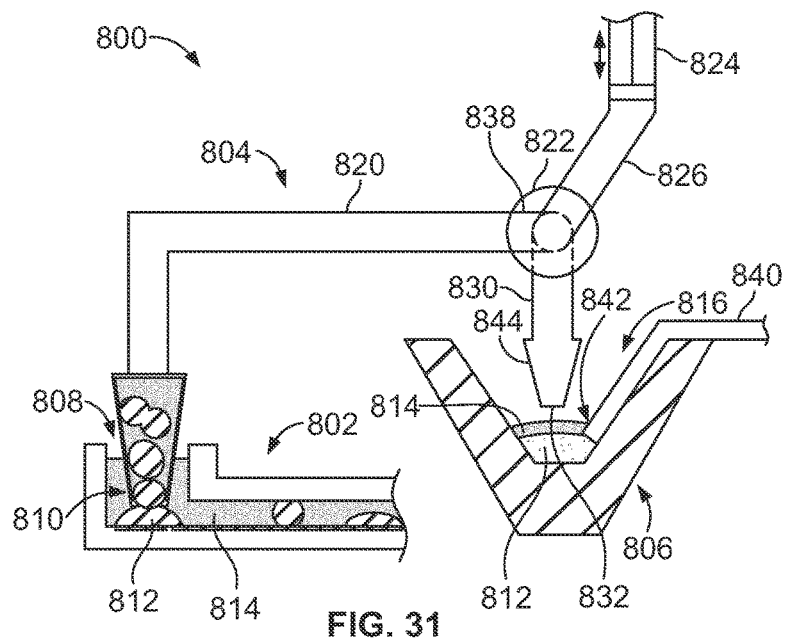
FIG. 31 is a schematic view of a system formed in accordance with an embodiment.

FIG. 31 is a schematic view of a system 800. The system 800 is configured to prepare a biological (or chemical) substance-of-interest in immiscible liquids and separate the immiscible liquids such that the substance-of-interest may be used for a designated assay or other process. In particular embodiments, the system 800 is configured to automatically prepare a library for SBS sequencing. However, in other embodiments, the system 800 may be used to generate a biological or chemical substance for other applications.

The system 800 includes a first device 802, a fluidic system 804, and a second device 806. The fluidic system 804 fluidly connects the first device 802 and the second device 806. In the illustrated embodiment, the first and second devices 802, 806 are a DF device 802 and a phase-separation device 806, respectively. The DF device 802 is configured to prepare the substance-of-interest. For instance, droplets of one or more liquids may be controlled through, for example, electrowetting operations conducted by the DV device 802. The DF device 802 includes an opening 808 from which a liquid mixture 810 may be removed. The liquid mixture 810 includes a first liquid 812 and a second liquid 814. The first and second liquids 812, 814 are immiscible liquids as described above. In the illustrated embodiment, the first liquid 812 is an aqueous solution (e.g., polar liquid) and the second liquid 814 is a filler liquid (e.g., non-polar liquid). Optionally, the liquid mixture 810 may include additional liquids that may or may not be immiscible with respect to the first liquid 812 and/or the second liquid 814.

The fluidic system 804 is configured to automatically remove the liquid mixture 810 from the opening 808 and deposit the liquid mixture 810 into a receiving cavity 816 of the phase-separation device 806. The removing and depositing of the liquid mixture 810 may be conducted in accordance with a predetermined schedule or sequence of operations. For example, the liquid mixture 810 may not be removed until a designated amount of the first liquid 812 has been prepared by the DF device 802. The phase-separation device 806 may be similar or identical to the phase-separation devices described herein.

The fluidic system 804 includes one or more valves and one or more pumps. Control of the valve(s) and pump(s) may be automated such that the fluidic system 804 transports the liquid mixture 810 to the receiving cavity 816 without pipetting by a user and in accordance with a predetermined schedule. Although not shown, the system 800 may include a system controller (e.g., processor or processors) that controls operation of the DF device 802, the valve(s), and the pump(s). The system controller may also control operation of an analysis system.

In the illustrated embodiment, the fluidic system 804 includes a fluid line 820, a control valve 822, and a pump 824. As shown, the fluid line 820 is a single conduit that fluidly connects the opening 806 and the control valve 822. However, it should be understood that the fluid line 820 may include a plurality of interconnected conduits (e.g., tubes, flow channels of MEMs devices, other valves, and the like). The control valve 822 may be configured to move between different states or positions. The control valve 822 may be in flow communication with the pump 824 in one or all of the different states. For example, in a first state, the control valve 822 fluidly connects the pump 824 and the fluid line 820 such that the pump 824 is capable of withdrawing the liquid mixture 810 from the DF device 802 and into a storage line 826 of the fluidic system 804. The storage line 826 extends between the control valve 822 and the pump 824 and may fluidly connect the pump 824 and the control valve 822. The pump 824 is configured to generate a negative pressure for drawing (or pulling) the designated volume into the storage line 826.

The storage line 826 is configured to have a designated volume of the liquid mixture 810 therein. After drawing a designated volume of the liquid mixture 810 into the storage line 826, the control valve 822 may be controlled to change from the first state to the second state. For example, the control valve 822 may be rotated such that a valve port 838 moves from being in flow communication with the fluid line 820 to being in flow communication with a depositing line 830 of the fluidic system 804. The depositing line 830 includes a nozzle 844 that is disposed within or adjacent to the receiving cavity 816. In the second state, the control valve 822 fluidly connects the storage line 826 and the depositing line 830. The nozzle 844 has an outlet 832 that is positioned to deposit the liquid mixture 810 into the receiving cavity 816. More specifically, when the control value 822 is in the second state, the pump 824 may generate a positive pressure that drives the liquid mixture 810 through the outlet 832 and into the receiving cavity 816. When the liquid mixture 810 is deposited into the receiving cavity 816, the phase-separation device 802 may separate the first and second liquids 812, 814. For example, the second liquid 814 may be absorbed into a porous membrane of the phase-separation device 802 such that the first liquid 812 remains within the receiving cavity 816 as described above.

Optionally, the system 800 may include a downstream line 840 that is configured to withdraw the first liquid 812 from the receiving cavity 814 after a designated time period or when a designated condition has been satisfied (e.g., a designated volume of the first liquid 812 has been achieved). For example, a nozzle 842 of the downstream line 840 may be in flow communication with a pump (not shown) that generates negative pressure to draw the first liquid 812 into the downstream line 840. The first liquid 812 may be directed through a fluidic network to transfer the first liquid 812 to a designated space, such as within an analysis system. In an exemplary embodiment, the analysis system is an SBS system.

In some embodiments, the system 800 is configured to repeatedly deposit volumes of the liquid mixture 810 into the receiving cavity 804 prior to the first liquid 812 being withdrawn from the receiving cavity 804. In such embodiments, a number of liquids may be collected within the receiving cavity 804. These liquids may be, for example, resistant to flowing into the porous membrane. The liquids that do not flow into the porous membrane may be miscible with respect to each other or immiscible. The liquids in the receiving cavity 804 may then be removed through the fluid line 840.

Figure 32:
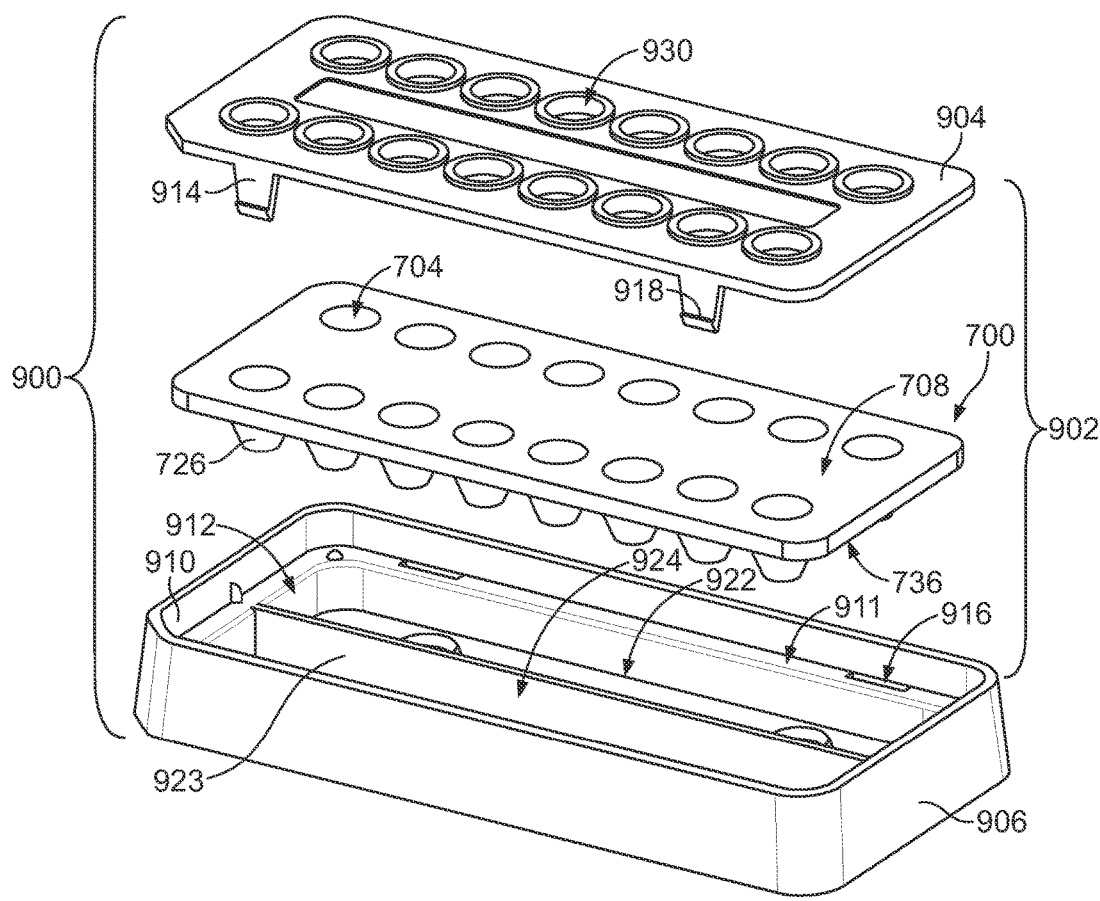
FIG. 32 is an exploded view of an assembly in accordance with an embodiment that includes the phase-separation device of FIG. 27.
Figure 33:
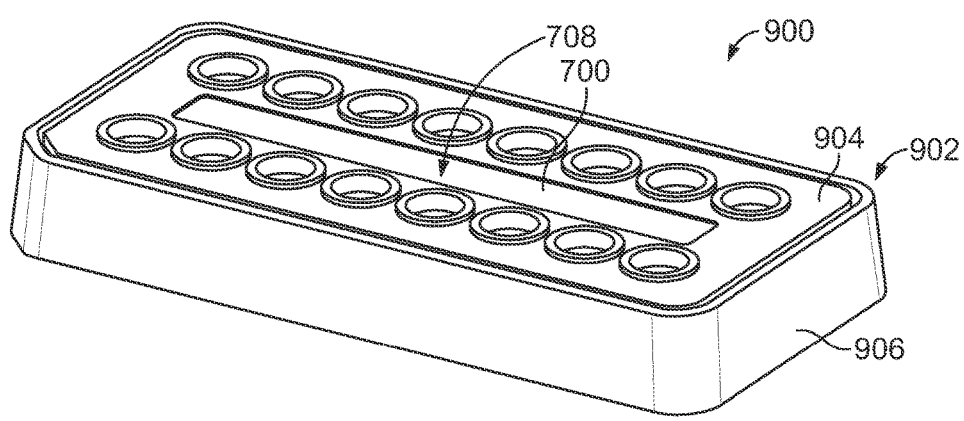
FIG. 33 is a perspective view of the fully constructed assembly in FIG. 32.

FIG. 32 is an exploded view of a cartridge assembly 900 in accordance with an embodiment that includes the phase-separation device 700. FIG. 33 is a perspective view of the cartridge assembly 900 when fully constructed. The cartridge assembly 900 may also be referred to as a phase-separation assembly. The cartridge assembly 900 includes a discrete support structure or sub-assembly 902 that is configured to hold the phase-separation device 700. The support structure 902 may increase a structural integrity (e.g., strength) of the phase-separation device 700 such that the phase-separation device 700 is less likely to break during transfer (e.g., shipping), storage, and/or use. In the illustrated embodiment, the support structure 902 includes a cover 904 and a base 906. When fully assembled, the cover 904 is positioned along the operating side 708, and the base 906 is positioned along the mounting side 736 (FIG. 32). The cover 904 and/or the base 906 may comprise a rigid material, such as plastic and/or metal.

In the illustrated embodiment, the cover 904 and the base 906 are configured to couple to each other with the phase-separation device 700 therebetween. The cover 904, the phase-separation device 700, and the base 906 may have a sandwich-like configuration. The base 906 includes a base wall 910 that defines a holding cavity 912 of the base 906 that is configured to receive the phase-separation device 700 and the cover 904. The base 906 may also include a base ledge 911 (FIG. 32) that is positioned within the holding cavity 912. The phase-separation device 700 may be configured to rest upon the base ledge 911 such that the filter bodies 726 (FIG. 32) are suspended within the holding cavity 912 during operation. Alternatively, the filter bodies 726 may engage an interior bottom surface of the base 906 that defines the holding cavity 912.

The base wall 910 may surround corresponding perimeters of the phase-separation device 700 and the cover 904. The base 906 and the cover 904 are configured to form an frictional engagement (e.g., interference fit or snap-fit) and may include complementary features for coupling to one another. In the illustrated embodiment shown in FIG. 32, the cover 904 includes tabs or legs 914 and the base 906 includes slots 916 that are sized and shaped to receive the tabs 914. After the phase-separation device 700 is positioned within the holding cavity 912, the cover 904 may be mounted onto the base 906 with the phase-separation device 700 therebetween. As the cover 904 is mounted, the tabs 914 may engage the base wall 910 and be deflected inward. After the tabs 914 are inserted into the slots 916, the tabs 914 may flex outwardly. As shown, the tabs 914 may include grip features 918 that engage the base 904. The grip features 918 may prevent the cover 904 from being inadvertently removed from the phase-separation device 700 during operation or transport.

As shown in FIG. 32, the cover 904 includes passages or openings 930 that are positioned to align with the receiving cavities 704. The holding cavity 912 may include cavity channels 922, 924 that are separated by a dividing wall 923 and form portions of the holding cavity 912. Each of the cavity channels 922, 924 may be sized and shaped to receive a corresponding row or column of the filter bodies 726. In some embodiments, the liquid flowing into the porous membrane of the phase-separation device 700 may be permitted to exit the filter bodies 726 and pool within the holding cavity 912.

In some embodiments, the cartridge assembly 900 is a single use item that is disposed of after one use. In other embodiments, the base 906 and cover 904 of the discrete support structure 902 may be separable such that the support structure 902 may be re-used with other phase-separation devices 700.

Figure 34:
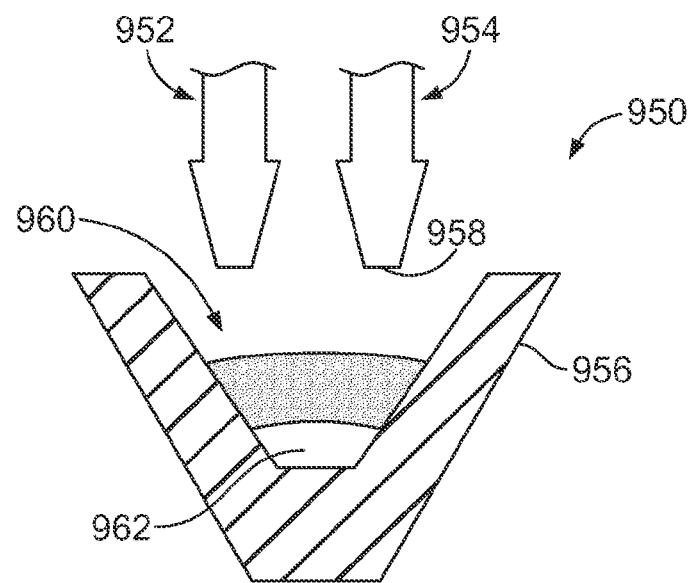
FIG. 34 is a schematic view of a system formed in accordance with an embodiment.
Figure 35:
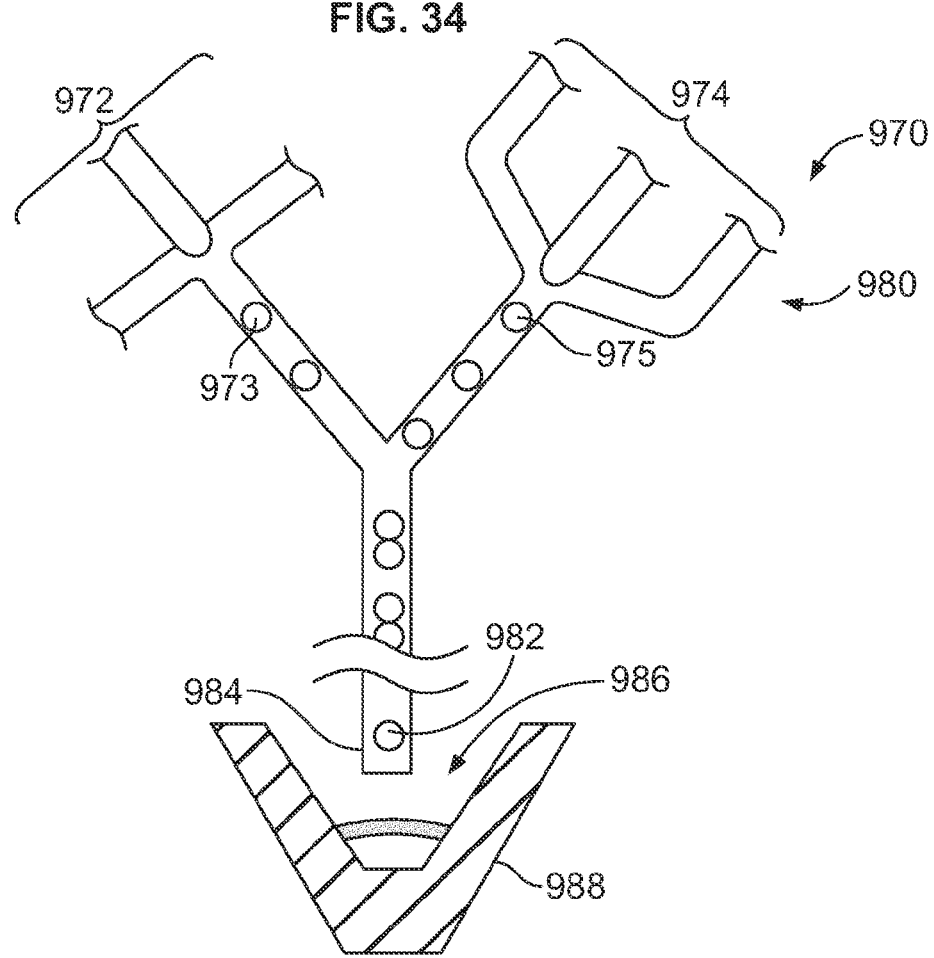
FIG. 35 is a schematic view of a system formed in accordance with an embodiment.

FIGS. 34 and 35 illustrate schematic views of respective systems in which emulsion droplets are pooled within a common receiving cavity of a phase-separation device. FIG. 34 illustrates a system 950 that includes first and second fluidic systems 952, 954 and a phase-separation device 956 that is positioned to receive first and second liquid mixtures from the fluidic systems 952, 954, respectively. The fluidic systems 952, 954 may be similar or identical to the fluidic system 804 (FIG. 31).

Each of the fluidic systems 952, 954 includes a corresponding outlet 958. The phase-separation device 956 is positioned such that a receiving cavity 960 of the phase-separation device 956 receives corresponding liquid mixtures therein. The liquid mixtures may include aqueous droplets or emulsion droplets. The liquid mixtures may separate such that the first liquids (e.g., aqueous liquids) pool together within the receiving cavity 960 to form a liquid pool 962. The second liquids of the liquid mixture may be the same or different liquids and may flow into the phase-separation device 956. Although not shown, the system 950 may optionally include a downstream line that is configured to automatically remove the liquid pool 962. In some embodiments, the phase-separation device 956 may be coupled to an agitation device (e.g., shaker, vibrator, etc.) that may agitate the phase-separation device 956 to facilitate breaking the aqueous droplets and/or allowing the aqueous droplets to join one another. In some embodiments, the liquid pool 962 may be subjected to certain conditions (e.g., thermal energy or other reactants) to allow designated reactions to occur within the receiving cavity 958. Although only a single receiving cavity 960 is shown in FIG. 34, it should be understood that the fluidic systems 952, 954 may deposit droplets of liquid mixtures into multiple receiving cavities.

FIG. 35 is a schematic view of a system 970 formed in accordance with an embodiment. The system 970 may be similar to systems that conduct digital PCR or other systems that generate emulsion droplets using microfluidic devices and, optionally, join the emulsion droplets to conduct designated reactions. Such embodiments may include a network of flow channels in which a non-polar liquid flows through one or more of the channels and an aqueous solution (or solutions) flows through one or more other channels. The channels intersect each other to form emulsion droplets. Such technology and related systems are described in greater detail in US 2009/0239308 A1; US 2009/0131543 A1; US 2010/0173394 A1; US 2010/0137163 A1; US 2013/0099018 A1; US 2013/0323732 A1; US 2014/0272996 A1; US 2014/0216579 A1; and US 2014/0256595 A1, each of which is incorporated herein by reference in its entirety.

For example, the system 970 includes a fluidic network 980 having a plurality flow channels that include a first channel group 972 and a second channel group 974. The first channel group 972 includes a plurality of intersecting channels that are configured to create emulsion droplets 973. The emulsion droplets 973 may include, for example, a mix of reactants for conducting PCR. The second channel group 974 includes a plurality of intersecting channels that are configured to create emulsion droplets 975. The emulsion droplets 975 may include, for example, genomic DNA. The DNA may be dispersed within an aqueous solution 978 such that each emulsion droplet 975 includes, on average, a single nucleic acid fragment. It should be understood, however, that the emulsion droplets 973, 975 may include other types of reactants (e.g., reagents, enzymes) and/or samples.

As shown, flow of the liquids through the fluidic network 980 is configured such that the emulsion droplets 973 typically join only one of the emulsion droplets 975 to form a combined droplet 982. As the combined droplets 982 flow through the system 970, the combined droplets may be subjected to designated conditions and/or combine with droplets containing other reactants. At an end of the fluidic network 980, a downstream channel 984 may direct the combined droplets 982 into a receiving cavity 986 of a phase-separation device 988. In some embodiments, a single combined droplet 982 may be directed into the receiving cavity 986. In other embodiments, a plurality of combined droplets 982 may be pooled within the receiving cavity 986. Optionally, a second downstream line (not shown) from another fluidic network may direct combined droplets into the receiving cavity 984 in a similar manner as described above with respect to FIG. 34. Optionally, a downstream line (not shown) may be disposed within the receiving cavity 986 and configured to direct flow of the pooled liquid to another stage of an assay protocol.

It should be understood that the particular embodiments set forth herein, including the embodiments shown in FIGS. 16-26, are intended to be illustrative and not restrictive. For example, one or more of the dimensions noted in FIGS. 16-26 may be increased or decreased while one or more dimensions remain the same. As another example, the dimensions may increase or decrease in proportion with respect to one another such that that size ratios are maintained. The angles may be increased or decreased. Accordingly, modifications may be made to adapt embodiments to particular applications.

In an embodiment, a method is provided. The method includes providing a phase-separation device including a porous membrane that has a filter surface. The filter surface has a non-planar contour that forms a receiving cavity. The method also includes depositing a liquid mixture into the receiving cavity of the porous membrane. The liquid mixture includes a polar liquid and a non-polar liquid that are immiscible with respect to each other. The filter surface along the receiving cavity is configured to impede flow of the polar liquid through the filter surface and permit flow of the non-polar liquid into the porous membrane. The method also includes permitting the non-polar liquid to flow into the porous membrane. The polar liquid forms a droplet within the receiving cavity as the non-polar liquid flows into the porous membrane.

In one aspect, the polar liquid may be denser than the non-polar liquid.

In another aspect, the filter surface may be hydrophobic.

In another aspect, the porous membrane may be hydrophobic.

In another aspect, the filter surface may contact the liquid mixture at different depths of the receiving cavity.

In another aspect, the receiving cavity may have a concave shape.

In another aspect, the receiving cavity may be conical.

In another aspect, at least a portion of the filter surface may have a radius of curvature.

In another aspect, a majority of the filter surface may have a slope that changes a depth of the receiving cavity at a linear rate.

In another aspect, the receiving cavity may have a bottom representing a maximum depth of the receiving cavity. The bottom may be located at a center of the receiving cavity.

In another aspect, the receiving cavity may have a bottom representing a maximum depth of the receiving cavity. The filter surface may have a slope that increases from the bottom to an access opening of the receiving cavity.

In another aspect, the receiving cavity may have a bottom representing a maximum depth of the receiving cavity. The filter surface may be rotationally symmetrical about a cavity axis that extends through the bottom.

In another aspect, the receiving cavity may have an access opening that is defined by a cavity edge. The receiving cavity may have a maximum depth that is less than a maximum diameter of the access opening. Optionally, an aspect ratio of the maximum diameter to the maximum depth may be 1.5:1 or more. Optionally, the aspect ratio of the maximum diameter to the maximum depth may be 2:1 or more.

In another aspect, the receiving cavity may have an access opening that is defined by a cavity edge. The receiving cavity may have a maximum depth that is greater than a maximum diameter of the access opening. Optionally, an aspect ratio of the maximum diameter to the maximum depth may be 1:2 or less. Optionally, the aspect ratio of the maximum diameter to the maximum depth may be 1:3 or less.

In another aspect, the droplet may form a contact angle with respect to the filter surface. The contact angle may be equal to or greater than 60°. Optionally, the contact angle may be equal to or greater than 65°. Optionally, the contact angle may be equal to or greater than 70°. Optionally, the contact angle may be equal to or greater than 75°. Optionally, the contact angle may be equal to or greater than 80°. Optionally, the contact angle may be equal to or greater than 85°.

In another aspect, the droplet may have an exterior surface that has a convex contour.

In another aspect, the porous membrane may include an absorption region that is positioned adjacent to the receiving cavity. The absorption region may have a volume that is greater than a volume of the receiving cavity.

In another aspect, the porous membrane may be defined between the filter surface and an outer surface. The outer surface may permit the non-polar liquid to flow out of the porous membrane.

In another aspect, the porous membrane may include polytetrafluoroethylene (PTFE). Optionally, the porous membrane may consist essentially of polytetrafluoroethylene (PTFE). Optionally, the porous membrane may consist of polytetrafluoroethylene (PTFE).

In another aspect, the porous membrane may have a pore size that is between and 10 µm and 50 µm.

In another aspect, the porous membrane may have a pore size that is between 20 µm and 40 µm.

In another aspect, the porous membrane may have a porosity that is between 40% and 70%.

In another aspect, the porous membrane may have a porosity that is between 50% and 65%.

In another aspect, at least 75% of the non-polar liquid may be removed from the receiving cavity within 30 seconds.

In another aspect, at least 85% of the non-polar liquid may be removed from the receiving cavity within 30 seconds.

In another aspect, at least 95% of the non-polar liquid may be removed from the receiving cavity within 30 seconds.

In another aspect, at least 98% of the non-polar liquid may be removed from the receiving cavity within 30 seconds.

In another aspect, at least 85% of the non-polar liquid may be removed from the receiving cavity within 20 seconds.

In another aspect, at least 85% of the non-polar liquid may be removed from the receiving cavity within 10 seconds.

In another aspect, at least 85% of the non-polar liquid may be removed from the receiving cavity within 5 seconds.

In another aspect, depositing the liquid mixture into receiving cavity includes depositing a measured volume.

In another aspect, each of the polar liquid and the non-polar liquid may have a corresponding volume when the liquid mixture is deposited into the receiving cavity. The corresponding volume of the non-polar liquid may be greater than the corresponding volume of the polar liquid.

In another aspect, a ratio of the corresponding volume of the non-polar liquid to the corresponding volume of the polar liquid may be at least 2:1.

In another aspect, a ratio of the corresponding volume of the non-polar liquid to the corresponding volume of the polar liquid may be at least 5:1.

In another aspect, a ratio of the corresponding volume of the non-polar liquid to the corresponding volume of the polar liquid may be at least 10:1.

In another aspect, the droplet may be centrally located within the receiving cavity.

In another aspect, the method further comprises removing the droplet from the receiving cavity. Optionally, at most 25% of a volume of the removed droplet is the non-polar liquid. Optionally, at most 10% of a volume of the removed droplet is the non-polar liquid. Optionally, at most 5% of a volume of the removed droplet is the non-polar liquid.

In another aspect, permitting the non-polar liquid to flow into the porous membrane does not include moving the phase-separation device to facilitate flowing the non-polar liquid into the porous membrane.

In another aspect, permitting the non-polar liquid to flow into the porous membrane does not include agitating the phase-separation device or generating a centripetal force to cause the non-polar liquid to flow into the porous membrane.

In another aspect, permitting the non-polar liquid to flow into the porous membrane includes moving the phase-separation device to facilitate flowing the non-polar liquid into the porous membrane.

In another aspect, permitting the non-polar liquid to flow into the porous membrane includes at least one of agitating the phase-separation device or generating a centripetal force to cause the non-polar liquid to flow into the porous membrane.

In another aspect, the phase-separation device includes a plurality of the receiving cavities and the step of depositing the liquid mixture may include depositing the liquid mixture into each of the receiving cavities.

In another aspect, the receiving cavities may include a first receiving cavity and a second receiving cavity. The polar liquid of the liquid mixture in the first receiving cavity may be different than the polar liquid of the liquid mixture in the second receiving cavity. Alternatively, the polar liquids may have the same or essentially the same composition.

In another aspect, the filter surface of the porous membrane may form each of the receiving cavities.

In another aspect, the phase-separation device has a height that is greater than a width or length of the phase-separation device.

In another aspect, the phase-separation device includes a tube and the porous membrane is sized and shaped to be inserted into the tube.

In another aspect, the method may also include removing the liquid mixture from a digital fluidics (DF) device prior to depositing the liquid mixture.

In another aspect, the method may also include generating a biological sample utilizing a DF device. The biological sample may be within the polar liquid of the liquid mixture. Optionally, the biological sample may include a library of fragmented nucleic acids.

In another aspect, the method may also include removing the droplet from the receiving cavity and using the droplet to conduct designated biochemical reactions.

In another aspect, providing the phase-separation device includes orienting the phase-separation device such that gravity holds the liquid mixture within the receiving cavity.

In an embodiment, a phase-separation device is provided that includes a porous membrane having a filter surface. The filter surface may have a non-planar contour that forms a receiving cavity. The filter surface is configured to impede flow of a polar liquid into the porous membrane and permit flow of a non-polar liquid into the porous membrane.

In one aspect, the filter surface may be hydrophobic.

In another aspect, the porous membrane may be hydrophobic.

In another aspect, the filter surface may be shaped to contact the liquid mixture at different depths.

In another aspect, the receiving cavity may have a concave shape.

In another aspect, the receiving cavity may be conical.

In another aspect, at least a portion of the filter surface may have a radius of curvature.

In another aspect, a majority of the filter surface may have a slope that changes the depth at a linear rate.

In another aspect, the receiving cavity may have a bottom representing a maximum depth of the receiving cavity. The bottom may be located at a center of the receiving cavity.

In another aspect, the receiving cavity may have a bottom representing a maximum depth of the receiving cavity. The filter surface may have a slope that increases from the bottom to an access opening of the receiving cavity.

In another aspect, the receiving cavity may have an access opening that is defined by a cavity edge. The receiving cavity may have a maximum depth that is less than a maximum diameter of the access opening.

In another aspect, an aspect ratio of the maximum diameter to the maximum depth is 1.5:1 or more. Optionally, the aspect ratio of the maximum diameter to the maximum depth is 2:1 or more.

In another aspect, the receiving cavity may have an access opening that is defined by a cavity edge. The receiving cavity may have a maximum depth that is greater than a maximum diameter of the access opening. Optionally, an aspect ratio of the maximum diameter to the maximum depth is 1:2 or less. Optionally, the aspect ratio of the maximum diameter to the maximum depth is 1:3 or less.

In another aspect, the porous membrane may include an absorption region that is positioned adjacent to the receiving cavity. The absorption region may have a volume that is greater than a volume of the receiving cavity.

In another aspect, the porous membrane may be defined between the filter surface and an outer surface. The outer surface may be configured to permit the non-polar liquid to flow out of the porous membrane.

In another aspect, the porous membrane may include polytetrafluoroethylene (PTFE). Optionally, the porous membrane may consist essentially of polytetrafluoroethylene (PTFE). Optionally, the porous membrane may consist of polytetrafluoroethylene (PTFE).

In another aspect, the porous membrane may have a pore size that is between and 10 µm and 50 µm.

In another aspect, the porous membrane may have a pore size that is between 20 µm and 40 µm.

In another aspect, the porous membrane may have a porosity that is between 40% and 70%.

In another aspect, the porous membrane may have a porosity that is between 50% and 65%.

In another aspect, the phase-separation device includes a plurality of the receiving cavities.

In another aspect, the filter surface of the porous membrane may form each of the receiving cavities.

In another aspect, the phase-separation device may have a height that is greater than a width or length of the phase-separation device.

In another aspect, the phase-separation device may include a tube and the porous membrane may be sized and shaped to be inserted into the tube.

In an embodiment, a method is provided that includes providing a phase-separation device including a porous membrane having a filter surface. The filter surface has a non-planar contour that forms a receiving cavity. The method also includes depositing a liquid mixture into the receiving cavity of the porous membrane. The liquid mixture includes a first liquid and a second liquid that are immiscible with respect to each other. The filter surface along the receiving cavity is configured to impede flow of the first liquid through the filter surface and permit flow of the second liquid into the porous membrane. The method also includes permitting the second liquid to flow into the porous membrane. The first liquid forms a droplet within the receiving cavity as the second liquid flows into the porous membrane.

In one aspect, the first liquid may be a polar liquid and the second liquid may be a non-polar liquid. Optionally, at least one of the filter surface and the porous membrane is hydrophobic.

In another aspect, the first liquid may be a non-polar liquid and the second liquid may be a polar liquid. Optionally, at least one of the filter surface and the porous membrane is hydrophilic.

In an embodiment, an assay system is provided that includes a sample preparation system configured to prepare a liquid mixture having a polar liquid and a non-polar liquid that are immiscible with respect to each other. The assay system may also include a phase-separation device including a porous membrane having a filter surface. The filter surface has a non-planar contour that forms a receiving cavity configured to receive the liquid mixture. The filter surface along the receiving cavity is configured to impede flow of the polar liquid through the filter surface and permit flow of the non-polar liquid into the porous membrane such that the polar liquid forms a droplet within the receiving cavity as the non-polar liquid flows into the porous membrane.

In one aspect, the assay system includes a flow-facilitating device that is configured to move the phase-separation device to facilitate flow of the non-polar liquid.

In an embodiment, an assay system is provided that includes a phase-separation device including a porous membrane having a filter surface. The filter surface has a non-planar contour that forms a receiving cavity configured to receive a liquid mixture. The liquid mixture has a polar liquid and a non-polar liquid that are immiscible with respect to each other. The filter surface along the receiving cavity is configured to impede flow of the polar liquid through the filter surface and permit flow of the non-polar liquid into the porous membrane such that the polar liquid forms a droplet within the receiving cavity as the non-polar liquid flows into the porous membrane. The assay system also includes an analysis system configured to perform one or more assay protocols utilizing the droplet of the polar liquid.

In one aspect, the assay system also includes a flow-facilitating device that is configured to move the phase-separation device to facilitate flow of the non-polar liquid.

In an embodiment, an assay system is provided that includes a sample preparation system configured to prepare a liquid mixture having a first liquid and a second liquid that are immiscible with respect to each other. The assay system also includes a phase-separation device including a porous membrane having a filter surface. The filter surface has a non-planar contour that forms a receiving cavity configured to receive the liquid mixture. The filter surface along the receiving cavity is configured to impede flow of the first liquid through the filter surface and permit flow of the second liquid into the porous membrane such that the first liquid forms a droplet within the receiving cavity as the second liquid flows into the porous membrane.

In one aspect, the assay system also includes a flow-facilitating device that is configured to move the phase-separation device to facilitate flow of the second liquid.

In an embodiment, an assay system is provided that includes a phase-separation device that includes a porous membrane having a filter surface. The filter surface has a non-planar contour that forms a receiving cavity configured to receive a liquid mixture. The liquid mixture has a first liquid and a second liquid that are immiscible with respect to each other. The filter surface along the receiving cavity is configured to impede flow of the first liquid through the filter surface and permit flow of the second liquid into the porous membrane such that the first liquid forms a droplet within the receiving cavity as the second liquid flows into the porous membrane. The assay system also includes an analysis system configured to perform one or more assay protocols utilizing the droplet of the first liquid.

In one aspect, the assay system includes a flow-facilitating device that is configured to move the phase-separation device to facilitate flow of the second liquid.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements whether or not they have that property.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The patentable scope should, therefore, be determined with reference to the appended claims, along with the full scope of equivalents to which such claims are entitled.

As used in the description, the phrase "in an exemplary embodiment" and the like means that the described embodiment is just one example. The phrase is not intended to limit the inventive subject matter to that embodiment. Other embodiments of the inventive subject matter may not include the recited feature or structure. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A phase-separation method comprising:
providing a phase-separation device including a porous membrane having a filter surface, the filter surface having a non-planar contour that forms a receiving cavity;
depositing a liquid mixture into the receiving cavity of the porous membrane, the liquid mixture including a polar liquid and a non-polar liquid that are immiscible with respect to each other, the filter surface along the receiving cavity configured to impede flow of the polar liquid through the filter surface and permit flow of the non-polar liquid into the porous membrane; and
permitting the non-polar liquid to flow into the porous membrane, the filter surface along the receiving cavity configured so that the polar liquid forms a droplet within the receiving cavity as the non-polar liquid flows into the porous membrane.

2. The method of claim 1, wherein the polar liquid is denser than the non-polar liquid.

3. The method of claim 1, wherein the filter surface is hydrophobic.

4. The method of claim 1, wherein the filter surface contacts the liquid mixture at different depths of the receiving cavity.

5. The method of claim 1, wherein at least a portion of the filter surface has a radius of curvature.

6. The method of claim 1, wherein a majority of the filter surface has a slope that changes a depth of the receiving cavity at a linear rate.

7. The method of claim 1, wherein the receiving cavity has a bottom representing a maximum depth of the receiving cavity, the filter surface having a slope that increases from the bottom to an access opening of the receiving cavity.

8. The method of claim 1, wherein the receiving cavity has an access opening that is defined by a cavity edge, the receiving cavity having a maximum depth that is less than a maximum diameter of the access opening.

9. The method of claim 1, wherein the receiving cavity has an access opening that is defined by a cavity edge, the receiving cavity having a maximum depth that is greater than a maximum diameter of the access opening.

10. The method of claim 1, wherein the droplet forms a contact angle with respect to the filter surface, the contact angle being equal to or greater than 60°.

11. The method of claim 1, wherein the porous membrane includes an absorption region that is positioned adjacent to the receiving cavity, the absorption region having a volume that is greater than a volume of the receiving cavity.

12. The method of claim 1, wherein the porous membrane is defined between the filter surface and an outer surface, the outer surface permitting the non-polar liquid to flow out of the porous membrane.

13. The method of claim 1, wherein the porous membrane comprises polytetrafluoroethylene (PTFE).

14. The method of claim 1, wherein the porous membrane has a pore size that is between and 10 μm and 50 μm and wherein the porous membrane has a porosity that is between 40% and 70%.

15. The method of claim 1, wherein at least 85% of the non-polar liquid is removed from the receiving cavity within 20 seconds.

16. The method of claim 1, wherein a ratio of the corresponding volume of the non-polar liquid to the corresponding volume of the polar liquid is at least 5:1.

17. The method of claim 1, wherein the phase-separation device includes a plurality of the receiving cavities and the step of depositing the liquid mixture includes depositing the liquid mixture into each of the receiving cavities, wherein the receiving cavities include a first receiving cavity and a second receiving cavity, the polar liquid of the liquid mixture in the first receiving cavity being different than the polar liquid of the liquid mixture in the second receiving cavity.

18. The method of claim 1, wherein the phase-separation device includes a tube and the porous membrane is sized and shaped to be inserted into the tube.

19. The method of claim 1, further comprising removing the liquid mixture from a digital fluidics (DF) device prior to depositing the liquid mixture.

20. The method of claim 19, further comprising generating a biological sample utilizing the DF device, the biological sample being within the polar liquid of the liquid mixture.

21. The method of claim 20, wherein the biological sample includes a library of fragmented nucleic acids.

* * * * *